United States Patent
Ohlsson et al.

(10) Patent No.: US 10,161,886 B2
(45) Date of Patent: Dec. 25, 2018

(54) DETECTION OF SURFACE CONTAMINATION

(71) Applicant: FlatFrog Laboratories AB, Lund (SE)

(72) Inventors: Nicklas Ohlsson, Bunkeflostrand (SE); Tomas Christiansson, Torna-hällestad (SE)

(73) Assignee: FlatFrog Laboratories AB, Lund (SE)

( * ) Notice: Subject to any disclaimer, the term of this patent is extended or adjusted under 35 U.S.C. 154(b) by 0 days.

(21) Appl. No.: 15/317,360

(22) PCT Filed: Jun. 22, 2015

(86) PCT No.: PCT/SE2015/050724
§ 371 (c)(1),
(2) Date: Dec. 8, 2016

(87) PCT Pub. No.: WO2015/199602
PCT Pub. Date: Dec. 30, 2015

(65) Prior Publication Data
US 2017/0115235 A1    Apr. 27, 2017

(30) Foreign Application Priority Data
Jun. 27, 2014   (SE) .................................. 1450796

(51) Int. Cl.
*G01N 21/958*   (2006.01)
*G06F 3/041*   (2006.01)
(Continued)

(52) U.S. Cl.
CPC ........... *G01N 21/958* (2013.01); *G01N 21/59* (2013.01); *G01N 21/94* (2013.01); *G06F 3/0418* (2013.01);
(Continued)

(58) Field of Classification Search
CPC .. G01N 2021/945; G01N 21/59; G01N 21/94; G01N 21/958; G01N 2201/124;
(Continued)

(56) References Cited

U.S. PATENT DOCUMENTS

| 3,440,426 A | 4/1969 | Bush |
| 3,553,680 A | 1/1971 | Cooreman |

(Continued)

FOREIGN PATENT DOCUMENTS

| CN | 201233592 Y | 5/2009 |
| CN | 101644854 A | 2/2010 |

(Continued)

OTHER PUBLICATIONS

Ahn, Y., et al., "A slim and wide multi-touch tabletop interface and its applications," BigComp2014, IEEE, 2014, in 6 pages.
(Continued)

*Primary Examiner* — Tri T Ton
(74) *Attorney, Agent, or Firm* — Knobbe, Martens, Olson & Bear, LLP

(57) ABSTRACT

A device implements a method for detecting contamination of an FTIR-based panel. The apparatus generates projection signals representing detection lines that have propagated on a plurality of propagation paths by total internal reflection (TIR) inside a transmissive panel such that contamination on the panel surface causes attenuation (frustration) of at least one of the projection signals. The device generates a transmission value for each detection line in the transmissive panel, and determines the presence of contamination on the surface of the panel by comparing the transmission values according to at least one of the presented comparison techniques.

15 Claims, 11 Drawing Sheets

(51) Int. Cl.
*G06F 3/042* (2006.01)
*G01N 21/59* (2006.01)
*G01N 21/94* (2006.01)

(52) U.S. Cl.
CPC ..... *G06F 3/0421* (2013.01); *G01N 2021/945* (2013.01); *G01N 2201/124* (2013.01); *G06F 2203/04109* (2013.01)

(58) Field of Classification Search
CPC ......... G06F 2203/04109; G06F 3/0418; G06F 3/0421
USPC ............................ 356/429–448, 237.1–239.8
See application file for complete search history.

(56) References Cited

U.S. PATENT DOCUMENTS

| | | |
|---|---|---|
| 3,673,327 A | 6/1972 | Johnson et al. |
| 4,129,384 A | 12/1978 | Walker et al. |
| 4,180,702 A | 12/1979 | Sick et al. |
| 4,209,255 A | 6/1980 | Heynau et al. |
| 4,213,707 A | 7/1980 | Evans, Jr. |
| 4,254,333 A | 3/1981 | Bergström |
| 4,254,407 A | 3/1981 | Tipon |
| 4,294,543 A | 10/1981 | Apple et al. |
| 4,346,376 A | 8/1982 | Mallos |
| 4,420,261 A | 12/1983 | Barlow et al. |
| 4,484,179 A | 11/1984 | Kasday |
| 4,507,557 A | 3/1985 | Tsikos |
| 4,521,112 A | 6/1985 | Kuwabara et al. |
| 4,542,375 A | 9/1985 | Alles et al. |
| 4,550,250 A | 10/1985 | Mueller et al. |
| 4,593,191 A | 6/1986 | Alles |
| 4,673,918 A | 6/1987 | Adler et al. |
| 4,688,933 A | 8/1987 | Lapeyre |
| 4,688,993 A | 8/1987 | Ferris et al. |
| 4,692,809 A | 9/1987 | Beining et al. |
| 4,710,760 A | 12/1987 | Kasday |
| 4,736,191 A | 4/1988 | Matzke et al. |
| 4,737,626 A | 4/1988 | Hasegawa |
| 4,746,770 A | 5/1988 | McAvinney |
| 4,752,655 A | 6/1988 | Tajiri et al. |
| 4,772,763 A | 9/1988 | Garwin et al. |
| 4,782,328 A | 11/1988 | Denlinger |
| 4,812,833 A | 3/1989 | Shimauchi |
| 4,837,430 A | 6/1989 | Hasegawa |
| 4,868,912 A | 9/1989 | Doering |
| 4,891,829 A | 1/1990 | Deckman et al. |
| 4,933,544 A | 6/1990 | Tamaru |
| 4,949,079 A | 8/1990 | Loebner |
| 4,986,662 A | 1/1991 | Bures |
| 4,988,983 A | 1/1991 | Wehrer |
| 5,065,185 A | 11/1991 | Powers et al. |
| 5,073,770 A | 12/1991 | Lowbner |
| 5,105,186 A | 4/1992 | May |
| 5,159,322 A | 10/1992 | Loebner |
| 5,166,668 A | 11/1992 | Aoyagi |
| 5,227,622 A | 7/1993 | Suzuki |
| 5,248,856 A | 9/1993 | Mallicoat |
| 5,254,407 A | 10/1993 | Sergerie et al. |
| 5,345,490 A | 9/1994 | Finnigan et al. |
| 5,383,022 A | 1/1995 | Kaser |
| 5,483,261 A | 1/1996 | Yasutake |
| 5,484,966 A | 1/1996 | Segen |
| 5,499,098 A | 3/1996 | Ogawa |
| 5,502,568 A | 3/1996 | Ogawa et al. |
| 5,525,764 A | 6/1996 | Junkins et al. |
| 5,526,422 A | 6/1996 | Keen |
| 5,539,514 A * | 7/1996 | Shishido ............... G01N 21/94 356/237.4 |
| 5,570,181 A | 10/1996 | Yasuo et al. |
| 5,572,251 A | 11/1996 | Ogawa |
| 5,577,501 A | 11/1996 | Flohr et al. |
| 5,600,105 A | 2/1997 | Fukuzaki et al. |
| 5,672,852 A | 9/1997 | Fukuzaki et al. |
| 5,679,930 A | 10/1997 | Katsurahira |
| 5,686,942 A | 11/1997 | Ball |
| 5,688,933 A | 11/1997 | Evans et al. |
| 5,729,249 A | 3/1998 | Yasutake |
| 5,736,686 A | 4/1998 | Perret, Jr. et al. |
| 5,740,224 A | 4/1998 | Müller et al. |
| 5,764,223 A | 6/1998 | Chang et al. |
| 5,767,517 A | 6/1998 | Hawkins |
| 5,775,792 A | 7/1998 | Wiese |
| 5,945,980 A | 8/1999 | Moissev et al. |
| 5,945,981 A | 8/1999 | Paull et al. |
| 5,959,617 A | 9/1999 | Bird et al. |
| 6,061,177 A | 5/2000 | Fujimoto |
| 6,067,079 A | 5/2000 | Shieh |
| 6,122,394 A | 9/2000 | Neukermans et al. |
| 6,141,104 A | 10/2000 | Schulz et al. |
| 6,172,667 B1 | 1/2001 | Sayag |
| 6,227,667 B1 | 5/2001 | Halldorsson et al. |
| 6,229,529 B1 | 5/2001 | Yano et al. |
| 6,333,735 B1 | 12/2001 | Anvekar |
| 6,366,276 B1 | 4/2002 | Kunimatsu et al. |
| 6,380,732 B1 | 4/2002 | Gilboa |
| 6,380,740 B1 | 4/2002 | Laub |
| 6,390,370 B1 | 5/2002 | Plesko |
| 6,429,857 B1 | 8/2002 | Masters et al. |
| 6,452,996 B1 | 9/2002 | Hsieh |
| 6,476,797 B1 | 11/2002 | Kurihara et al. |
| 6,492,633 B2 | 12/2002 | Nakazawa et al. |
| 6,495,832 B1 | 12/2002 | Kirby |
| 6,504,143 B2 | 1/2003 | Koops et al. |
| 6,529,327 B1 | 3/2003 | Graindorge |
| 6,538,644 B1 | 3/2003 | Muraoka |
| 6,587,099 B2 | 7/2003 | Takekawa |
| 6,648,485 B1 | 11/2003 | Colgan et al. |
| 6,660,964 B1 | 12/2003 | Benderly |
| 6,664,498 B2 | 12/2003 | Forsman et al. |
| 6,664,952 B2 | 12/2003 | Iwamoto et al. |
| 6,690,363 B2 | 2/2004 | Newton |
| 6,707,027 B2 | 3/2004 | Liess et al. |
| 6,738,051 B2 | 5/2004 | Boyd et al. |
| 6,748,098 B1 | 6/2004 | Rosenfeld |
| 6,784,948 B2 | 8/2004 | Kawashima et al. |
| 6,799,141 B1 | 9/2004 | Stoustrup et al. |
| 6,806,871 B1 | 10/2004 | Yasue |
| 6,927,384 B2 | 8/2005 | Reime et al. |
| 6,940,286 B2 | 9/2005 | Wang et al. |
| 6,965,836 B2 | 11/2005 | Richardson |
| 6,972,753 B1 | 12/2005 | Kimura et al. |
| 6,985,137 B2 | 1/2006 | Kaikuranta |
| 7,042,444 B2 | 5/2006 | Cok |
| 7,084,859 B1 | 8/2006 | Pryor |
| 7,087,907 B1 * | 8/2006 | Lalovic ................ G01N 21/64 250/461.1 |
| 7,133,031 B2 | 11/2006 | Wang et al. |
| 7,176,904 B2 | 2/2007 | Satoh |
| 7,359,041 B2 | 4/2008 | Xie et al. |
| 7,397,418 B1 | 7/2008 | Doerry et al. |
| 7,432,893 B2 | 10/2008 | Ma et al. |
| 7,435,940 B2 | 10/2008 | Eliasson et al. |
| 7,442,914 B2 | 10/2008 | Eliasson et al. |
| 7,465,914 B2 | 12/2008 | Eliasson et al. |
| 7,613,375 B2 | 11/2009 | Shimizu |
| 7,629,968 B2 | 12/2009 | Miller et al. |
| 7,646,833 B1 | 1/2010 | He et al. |
| 7,653,883 B2 | 1/2010 | Hotelling et al. |
| 7,655,901 B2 | 2/2010 | Idzik et al. |
| 7,705,835 B2 | 4/2010 | Eikman |
| 7,847,789 B2 | 12/2010 | Kolmykov-Zotov et al. |
| 7,855,716 B2 | 12/2010 | McCreary et al. |
| 7,859,519 B2 | 12/2010 | Tulbert |
| 7,924,272 B2 | 4/2011 | Boer et al. |
| 7,932,899 B2 | 4/2011 | Newton et al. |
| 7,969,410 B2 | 6/2011 | Kakarala |
| 7,995,039 B2 | 8/2011 | Eliasson et al. |
| 8,013,845 B2 | 9/2011 | Ostergaard et al. |
| 8,031,186 B2 | 10/2011 | Ostergaard |
| 8,077,147 B2 | 12/2011 | Krah et al. |
| 8,093,545 B2 | 1/2012 | Leong et al. |
| 8,094,136 B2 | 1/2012 | Eliasson et al. |

(56) References Cited

U.S. PATENT DOCUMENTS

| | | |
|---|---|---|
| 8,094,910 B2 | 1/2012 | Xu |
| 8,149,211 B2 | 4/2012 | Hayakawa et al. |
| 8,218,154 B2 | 7/2012 | Østergaard et al. |
| 8,274,495 B2 | 9/2012 | Lee |
| 8,325,158 B2 | 12/2012 | Yatsuda et al. |
| 8,339,379 B2 | 12/2012 | Goertz et al. |
| 8,350,827 B2 | 1/2013 | Chung et al. |
| 8,384,010 B2 | 2/2013 | Hong et al. |
| 8,407,606 B1 | 3/2013 | Davidson et al. |
| 8,441,467 B2 | 5/2013 | Han |
| 8,445,834 B2 | 5/2013 | Hong et al. |
| 8,466,901 B2 | 6/2013 | Yen et al. |
| 8,482,547 B2 | 7/2013 | Cobon et al. |
| 8,542,217 B2 | 9/2013 | Wassvik et al. |
| 8,567,257 B2 | 10/2013 | Van Steenberge et al. |
| 8,581,884 B2 | 11/2013 | Fåhraeus et al. |
| 8,624,858 B2 | 1/2014 | Fyke et al. |
| 8,686,974 B2 | 4/2014 | Christiansson et al. |
| 8,692,807 B2 | 4/2014 | Føhraeus et al. |
| 8,716,614 B2 | 5/2014 | Wassvik |
| 8,727,581 B2 | 5/2014 | Saccomanno |
| 8,745,514 B1 | 6/2014 | Davidson |
| 8,780,066 B2 | 7/2014 | Christiansson et al. |
| 8,830,181 B1 | 9/2014 | Clark et al. |
| 8,860,696 B2 | 10/2014 | Wassvik et al. |
| 8,872,098 B2 | 10/2014 | Bergström et al. |
| 8,872,801 B2 | 10/2014 | Bergström et al. |
| 8,884,900 B2 | 11/2014 | Wassvik |
| 8,890,843 B2 | 11/2014 | Wassvik et al. |
| 8,890,849 B2 | 11/2014 | Christiansson et al. |
| 8,928,590 B1 | 1/2015 | El Dokor |
| 8,963,886 B2 | 2/2015 | Wassvik |
| 8,982,084 B2 | 3/2015 | Christiansson et al. |
| 9,024,916 B2 | 5/2015 | Christiansson |
| 9,035,909 B2 | 5/2015 | Christiansson |
| 9,063,617 B2 | 6/2015 | Eliasson et al. |
| 9,086,763 B2 | 7/2015 | Johansson et al. |
| 9,134,854 B2 | 9/2015 | Wassvik et al. |
| 9,158,401 B2 | 10/2015 | Christiansson |
| 9,158,415 B2 | 10/2015 | Song et al. |
| 9,213,445 B2 | 12/2015 | King et al. |
| 9,274,645 B2 | 3/2016 | Christiansson et al. |
| 9,317,168 B2 | 4/2016 | Christiansson et al. |
| 9,323,396 B2 | 4/2016 | Han et al. |
| 9,366,565 B2 | 6/2016 | Uvnäs |
| 9,377,884 B2 | 6/2016 | Christiansson et al. |
| 9,389,732 B2 | 7/2016 | Craven-Bartle |
| 9,411,444 B2 | 8/2016 | Christiansson et al. |
| 9,411,464 B2 | 8/2016 | Wallander et al. |
| 9,430,079 B2 | 8/2016 | Christiansson et al. |
| 9,442,574 B2 | 9/2016 | Fåhraeus et al. |
| 9,547,393 B2 | 1/2017 | Christiansson et al. |
| 9,552,103 B2 | 1/2017 | Craven-Bartle et al. |
| 9,557,846 B2 | 1/2017 | Baharav et al. |
| 9,588,619 B2 | 3/2017 | Christiansson et al. |
| 9,594,467 B2 | 3/2017 | Christiansson et al. |
| 9,626,018 B2 | 4/2017 | Christiansson et al. |
| 9,626,040 B2 | 4/2017 | Wallander et al. |
| 9,639,210 B2 | 5/2017 | Wallander et al. |
| 9,678,602 B2 | 6/2017 | Wallander |
| 9,684,414 B2 | 6/2017 | Christiansson et al. |
| 9,710,101 B2 | 7/2017 | Christiansson et al. |
| 2001/0002694 A1 | 6/2001 | Nakazawa et al. |
| 2001/0005004 A1 | 6/2001 | Shiratsuki et al. |
| 2001/0005308 A1 | 6/2001 | Oishi et al. |
| 2001/0030642 A1 | 10/2001 | Sullivan et al. |
| 2002/0067348 A1 | 6/2002 | Masters et al. |
| 2002/0075243 A1 | 6/2002 | Newton |
| 2002/0118177 A1 | 8/2002 | Newton |
| 2002/0158823 A1 | 10/2002 | Zavracky et al. |
| 2002/0158853 A1 | 10/2002 | Sugawara et al. |
| 2002/0163505 A1 | 11/2002 | Takekawa |
| 2003/0016450 A1 | 1/2003 | Bluemel et al. |
| 2003/0034439 A1 | 2/2003 | Reime et al. |
| 2003/0034935 A1 | 2/2003 | Amanai et al. |
| 2003/0048257 A1 | 3/2003 | Mattila |
| 2003/0052257 A1 | 3/2003 | Sumriddetchkajorn |
| 2003/0095399 A1 | 5/2003 | Grenda et al. |
| 2003/0107748 A1 | 6/2003 | Lee |
| 2003/0137494 A1 | 7/2003 | Tulbert |
| 2003/0156100 A1 | 8/2003 | Gettemy |
| 2003/0160155 A1 | 8/2003 | Liess |
| 2003/0210537 A1 | 11/2003 | Engelmann |
| 2003/0214486 A1 | 11/2003 | Roberts |
| 2004/0027339 A1 | 2/2004 | Schulz |
| 2004/0032401 A1 | 2/2004 | Nakazawa et al. |
| 2004/0090432 A1 | 5/2004 | Takahashi et al. |
| 2004/0130338 A1 | 7/2004 | Wang et al. |
| 2004/0174541 A1 | 9/2004 | Freifeld |
| 2004/0201579 A1 | 10/2004 | Graham |
| 2004/0212603 A1 | 10/2004 | Cok |
| 2004/0238627 A1 | 12/2004 | Silverbrook et al. |
| 2004/0239702 A1 | 12/2004 | Kang et al. |
| 2004/0245438 A1 | 12/2004 | Payne et al. |
| 2004/0252091 A1 | 12/2004 | Ma et al. |
| 2004/0252867 A1 | 12/2004 | Lan et al. |
| 2005/0012714 A1 | 1/2005 | Russo et al. |
| 2005/0041013 A1 | 2/2005 | Tanaka |
| 2005/0057903 A1 | 3/2005 | Choi |
| 2005/0073508 A1 | 4/2005 | Pittel et al. |
| 2005/0083293 A1 | 4/2005 | Dixon |
| 2005/0128190 A1 | 6/2005 | Ryynanen |
| 2005/0143923 A1 | 6/2005 | Keers et al. |
| 2005/0156914 A1 | 7/2005 | Lipman et al. |
| 2005/0162398 A1 | 7/2005 | Eliasson et al. |
| 2005/0179977 A1 | 8/2005 | Chui et al. |
| 2005/0200613 A1 | 9/2005 | Kobayashi et al. |
| 2005/0212774 A1 | 9/2005 | Ho et al. |
| 2005/0248540 A1 | 11/2005 | Newton |
| 2005/0253834 A1 | 11/2005 | Sakamaki et al. |
| 2005/0276053 A1 | 12/2005 | Nortrup et al. |
| 2006/0001650 A1 | 1/2006 | Robbins et al. |
| 2006/0001653 A1 | 1/2006 | Smits |
| 2006/0007185 A1 | 1/2006 | Kobayashi |
| 2006/0008164 A1 | 1/2006 | Wu et al. |
| 2006/0017706 A1 | 1/2006 | Cutherell et al. |
| 2006/0017709 A1 | 1/2006 | Okano |
| 2006/0033725 A1 | 2/2006 | Marggraff et al. |
| 2006/0038698 A1 | 2/2006 | Chen |
| 2006/0061861 A1 | 3/2006 | Munro et al. |
| 2006/0114237 A1 | 6/2006 | Crockett et al. |
| 2006/0132454 A1 | 6/2006 | Chen et al. |
| 2006/0139340 A1 | 6/2006 | Geaghan |
| 2006/0158437 A1 | 7/2006 | Blythe et al. |
| 2006/0170658 A1 | 8/2006 | Nakamura et al. |
| 2006/0202974 A1 | 9/2006 | Thielman |
| 2006/0227120 A1 | 10/2006 | Eikman |
| 2006/0255248 A1 | 11/2006 | Eliasson |
| 2006/0256092 A1 | 11/2006 | Lee |
| 2006/0279558 A1 | 12/2006 | Van Delden et al. |
| 2006/0281543 A1 | 12/2006 | Sutton et al. |
| 2006/0290684 A1 | 12/2006 | Giraldo et al. |
| 2007/0014486 A1 | 1/2007 | Schiwietz et al. |
| 2007/0024598 A1 | 2/2007 | Miller et al. |
| 2007/0034783 A1 | 2/2007 | Eliasson et al. |
| 2007/0038691 A1 | 2/2007 | Candes et al. |
| 2007/0052684 A1 | 3/2007 | Gruhlke et al. |
| 2007/0070056 A1 | 3/2007 | Sato et al. |
| 2007/0075648 A1 | 4/2007 | Blythe et al. |
| 2007/0120833 A1 | 5/2007 | Yamaguchi et al. |
| 2007/0125937 A1 | 6/2007 | Eliasson et al. |
| 2007/0152985 A1 | 7/2007 | Ostergaard et al. |
| 2007/0201042 A1 | 8/2007 | Eliasson et al. |
| 2007/0296688 A1 | 12/2007 | Nakamura et al. |
| 2008/0006766 A1 | 1/2008 | Oon et al. |
| 2008/0007540 A1 | 1/2008 | Ostergaard |
| 2008/0007541 A1 | 1/2008 | Eliasson et al. |
| 2008/0007542 A1 | 1/2008 | Eliasson et al. |
| 2008/0011944 A1 | 1/2008 | Chua et al. |
| 2008/0029691 A1 | 2/2008 | Han |
| 2008/0036743 A1 | 2/2008 | Westerman et al. |
| 2008/0062150 A1 | 3/2008 | Lee |
| 2008/0068691 A1 | 3/2008 | Miyatake |
| 2008/0074401 A1 | 3/2008 | Chung et al. |

(56) References Cited

U.S. PATENT DOCUMENTS

| | | |
|---|---|---|
| 2008/0088603 A1 | 4/2008 | Eliasson et al. |
| 2008/0121442 A1 | 5/2008 | Boer et al. |
| 2008/0122792 A1 | 5/2008 | Izadi et al. |
| 2008/0122803 A1 | 5/2008 | Izadi et al. |
| 2008/0130979 A1 | 6/2008 | Run et al. |
| 2008/0150846 A1 | 6/2008 | Chung et al. |
| 2008/0150848 A1 | 6/2008 | Chung et al. |
| 2008/0151126 A1 | 6/2008 | Yu |
| 2008/0158176 A1 | 7/2008 | Land et al. |
| 2008/0189046 A1 | 8/2008 | Eliasson et al. |
| 2008/0192025 A1 | 8/2008 | Jaeger et al. |
| 2008/0238433 A1 | 10/2008 | Joutsenoja et al. |
| 2008/0246388 A1 | 10/2008 | Cheon et al. |
| 2008/0252619 A1 | 10/2008 | Crockett et al. |
| 2008/0266266 A1 | 10/2008 | Kent et al. |
| 2008/0278460 A1 | 11/2008 | Arnett et al. |
| 2008/0284925 A1 | 11/2008 | Han |
| 2008/0291668 A1 | 11/2008 | Aylward et al. |
| 2008/0297482 A1 | 12/2008 | Weiss |
| 2009/0002340 A1 | 1/2009 | Van Genechten |
| 2009/0006292 A1 | 1/2009 | Block |
| 2009/0040786 A1 | 2/2009 | Mori |
| 2009/0066647 A1 | 3/2009 | Kerr et al. |
| 2009/0067178 A1 | 3/2009 | Huang et al. |
| 2009/0073142 A1 | 3/2009 | Yamashita et al. |
| 2009/0077501 A1 | 3/2009 | Partridge et al. |
| 2009/0085894 A1 | 4/2009 | Gandhi et al. |
| 2009/0091554 A1 | 4/2009 | Keam |
| 2009/0115919 A1 | 5/2009 | Tanaka et al. |
| 2009/0122020 A1 | 5/2009 | Eliasson et al. |
| 2009/0128508 A1 | 5/2009 | Sohn et al. |
| 2009/0135162 A1 | 5/2009 | Van De Wijdeven et al. |
| 2009/0143141 A1 | 6/2009 | Wells et al. |
| 2009/0153519 A1 | 6/2009 | Suarez Rovere |
| 2009/0161026 A1 | 6/2009 | Wu et al. |
| 2009/0168459 A1 | 7/2009 | Holman et al. |
| 2009/0187842 A1 | 7/2009 | Collins et al. |
| 2009/0189857 A1 | 7/2009 | Benko et al. |
| 2009/0189874 A1 | 7/2009 | Chene et al. |
| 2009/0189878 A1 | 7/2009 | Goertz et al. |
| 2009/0219256 A1 | 9/2009 | Newton |
| 2009/0229892 A1 | 9/2009 | Fisher et al. |
| 2009/0251439 A1 | 10/2009 | Westerman et al. |
| 2009/0256817 A1 | 10/2009 | Perlin et al. |
| 2009/0259967 A1 | 10/2009 | Davidson et al. |
| 2009/0267919 A1 | 10/2009 | Chao et al. |
| 2009/0273794 A1 | 11/2009 | Østergaard et al. |
| 2009/0278816 A1 | 11/2009 | Colson |
| 2009/0297009 A1 | 12/2009 | Xu et al. |
| 2010/0033444 A1 | 2/2010 | Kobayashi |
| 2010/0045629 A1 | 2/2010 | Newton |
| 2010/0060896 A1 | 3/2010 | Van De Wijdeven et al. |
| 2010/0066016 A1 | 3/2010 | Van De Wijdeven et al. |
| 2010/0066704 A1 | 3/2010 | Kasai |
| 2010/0073318 A1 | 3/2010 | Hu et al. |
| 2010/0078545 A1 | 4/2010 | Leong et al. |
| 2010/0079407 A1 | 4/2010 | Suggs et al. |
| 2010/0079408 A1 | 4/2010 | Leong et al. |
| 2010/0097345 A1 | 4/2010 | Jang et al. |
| 2010/0097348 A1 | 4/2010 | Park et al. |
| 2010/0097353 A1 | 4/2010 | Newton |
| 2010/0125438 A1 | 5/2010 | Audet |
| 2010/0127975 A1 | 5/2010 | Jensen |
| 2010/0134435 A1 | 6/2010 | Kimura et al. |
| 2010/0142823 A1 | 6/2010 | Wang et al. |
| 2010/0187422 A1 | 7/2010 | Kothari et al. |
| 2010/0193259 A1 | 8/2010 | Wassvik |
| 2010/0229091 A1 | 9/2010 | Homma et al. |
| 2010/0238139 A1 | 9/2010 | Goertz et al. |
| 2010/0245292 A1 | 9/2010 | Wu |
| 2010/0265170 A1 | 10/2010 | Norieda |
| 2010/0277436 A1 | 11/2010 | Feng et al. |
| 2010/0283785 A1 | 11/2010 | Satulovsky |
| 2010/0284596 A1 | 11/2010 | Miao et al. |
| 2010/0289754 A1 | 11/2010 | Sleeman et al. |
| 2010/0295821 A1 | 11/2010 | Chang et al. |
| 2010/0302196 A1 | 12/2010 | Han et al. |
| 2010/0302209 A1 | 12/2010 | Large |
| 2010/0302210 A1 | 12/2010 | Han et al. |
| 2010/0302240 A1 | 12/2010 | Lettvin |
| 2010/0315379 A1 | 12/2010 | Allard et al. |
| 2010/0321328 A1 | 12/2010 | Chang et al. |
| 2010/0322550 A1 | 12/2010 | Trott |
| 2011/0043490 A1 | 2/2011 | Powell et al. |
| 2011/0049388 A1 | 3/2011 | Delaney et al. |
| 2011/0050649 A1 | 3/2011 | Newton et al. |
| 2011/0051394 A1 | 3/2011 | Bailey |
| 2011/0068256 A1 | 3/2011 | Hong et al. |
| 2011/0069039 A1 | 3/2011 | Lee et al. |
| 2011/0069807 A1 | 3/2011 | Dennerlein et al. |
| 2011/0074725 A1 | 3/2011 | Westerman et al. |
| 2011/0074734 A1 | 3/2011 | Wassvik et al. |
| 2011/0074735 A1 | 3/2011 | Wassvik et al. |
| 2011/0090176 A1 | 4/2011 | Christiansson et al. |
| 2011/0102374 A1 | 5/2011 | Wassvik et al. |
| 2011/0115748 A1 | 5/2011 | Xu |
| 2011/0121323 A1 | 5/2011 | Wu et al. |
| 2011/0122075 A1 | 5/2011 | Seo et al. |
| 2011/0122091 A1 | 5/2011 | King et al. |
| 2011/0122094 A1 | 5/2011 | Tsang et al. |
| 2011/0134079 A1 | 6/2011 | Stark |
| 2011/0147569 A1 | 6/2011 | Drumm |
| 2011/0157095 A1 | 6/2011 | Drumm |
| 2011/0157096 A1 | 6/2011 | Drumm |
| 2011/0163996 A1 | 7/2011 | Wassvik et al. |
| 2011/0163997 A1 | 7/2011 | Kim |
| 2011/0163998 A1 | 7/2011 | Goertz et al. |
| 2011/0169780 A1 | 7/2011 | Goertz et al. |
| 2011/0175852 A1 | 7/2011 | Goertz et al. |
| 2011/0205186 A1 | 8/2011 | Newton et al. |
| 2011/0216042 A1 | 9/2011 | Wassvik et al. |
| 2011/0221705 A1 | 9/2011 | Yi et al. |
| 2011/0221997 A1 | 9/2011 | Kim et al. |
| 2011/0227036 A1 | 9/2011 | Vaufrey |
| 2011/0227874 A1 | 9/2011 | Fåhraeus et al. |
| 2011/0234537 A1 | 9/2011 | Kim et al. |
| 2011/0254864 A1 | 10/2011 | Tsuchikawa et al. |
| 2011/0261020 A1 | 10/2011 | Song et al. |
| 2011/0267296 A1 | 11/2011 | Noguchi et al. |
| 2011/0291989 A1 | 12/2011 | Lee |
| 2011/0298743 A1 | 12/2011 | Machida et al. |
| 2011/0309325 A1 | 12/2011 | Park et al. |
| 2011/0310045 A1 | 12/2011 | Toda et al. |
| 2012/0019448 A1 | 1/2012 | Pitkanen et al. |
| 2012/0026408 A1 | 2/2012 | Lee et al. |
| 2012/0038593 A1 | 2/2012 | Rönkä et al. |
| 2012/0062474 A1 | 3/2012 | Weishaupt et al. |
| 2012/0068973 A1 | 3/2012 | Christiansson et al. |
| 2012/0086673 A1 | 4/2012 | Chien et al. |
| 2012/0089348 A1 | 4/2012 | Perlin et al. |
| 2012/0110447 A1 | 5/2012 | Chen |
| 2012/0131490 A1 | 5/2012 | Lin et al. |
| 2012/0141001 A1 | 6/2012 | Zhang et al. |
| 2012/0146930 A1 | 6/2012 | Lee |
| 2012/0153134 A1 | 6/2012 | Bergström et al. |
| 2012/0154338 A1 | 6/2012 | Bergström et al. |
| 2012/0162142 A1 | 6/2012 | Christiansson et al. |
| 2012/0162144 A1 | 6/2012 | Fåhraeus et al. |
| 2012/0169672 A1 | 7/2012 | Christiansson |
| 2012/0181419 A1 | 7/2012 | Momtahan |
| 2012/0182266 A1 | 7/2012 | Han |
| 2012/0188206 A1 | 7/2012 | Sparf et al. |
| 2012/0191993 A1 | 7/2012 | Drader et al. |
| 2012/0200532 A1 | 8/2012 | Powell et al. |
| 2012/0200538 A1 | 8/2012 | Christiansson et al. |
| 2012/0212441 A1 | 8/2012 | Christiansson et al. |
| 2012/0217882 A1 | 8/2012 | Wong et al. |
| 2012/0249478 A1 | 10/2012 | Chang et al. |
| 2012/0256882 A1 | 10/2012 | Christiansson et al. |
| 2012/0268403 A1 | 10/2012 | Christiansson |
| 2012/0268427 A1 | 10/2012 | Slobodin |
| 2012/0274559 A1 | 11/2012 | Mathai et al. |
| 2012/0305755 A1 | 12/2012 | Hong et al. |
| 2013/0021300 A1 | 1/2013 | Wassvik |

(56) References Cited

U.S. PATENT DOCUMENTS

| | | |
|---|---|---|
| 2013/0021302 A1 | 1/2013 | Drumm |
| 2013/0027404 A1 | 1/2013 | Sarnoff |
| 2013/0044073 A1 | 2/2013 | Christiansson et al. |
| 2013/0055080 A1 | 2/2013 | Komer et al. |
| 2013/0076697 A1 | 3/2013 | Goertz et al. |
| 2013/0082980 A1 | 4/2013 | Gruhlke et al. |
| 2013/0107569 A1 | 5/2013 | Suganuma |
| 2013/0113715 A1 | 5/2013 | Grant et al. |
| 2013/0120320 A1 | 5/2013 | Liu et al. |
| 2013/0125016 A1 | 5/2013 | Pallakoff et al. |
| 2013/0127790 A1 | 5/2013 | Wassvik |
| 2013/0135258 A1 | 5/2013 | King et al. |
| 2013/0135259 A1 | 5/2013 | King et al. |
| 2013/0141388 A1 | 6/2013 | Ludwig et al. |
| 2013/0154983 A1 | 6/2013 | Christiansson et al. |
| 2013/0155027 A1 | 6/2013 | Holmgren et al. |
| 2013/0181896 A1 | 7/2013 | Gruhlke et al. |
| 2013/0187891 A1 | 7/2013 | Eriksson et al. |
| 2013/0201142 A1 | 8/2013 | Suarez Rovere |
| 2013/0222346 A1 | 8/2013 | Chen et al. |
| 2013/0241887 A1 | 9/2013 | Sharma |
| 2013/0249833 A1 | 9/2013 | Christiansson et al. |
| 2013/0269867 A1 | 10/2013 | Trott |
| 2013/0275082 A1 | 10/2013 | Follmer et al. |
| 2013/0285920 A1 | 10/2013 | Colley |
| 2013/0285968 A1 | 10/2013 | Christiansson et al. |
| 2013/0300716 A1 | 11/2013 | Craven-Bartle et al. |
| 2013/0307795 A1 | 11/2013 | Suarez Rovere |
| 2013/0342490 A1 | 12/2013 | Wallander et al. |
| 2014/0002400 A1 | 1/2014 | Christiansson et al. |
| 2014/0028575 A1 | 1/2014 | Parivar et al. |
| 2014/0028604 A1 | 1/2014 | Morinaga et al. |
| 2014/0028629 A1 | 1/2014 | Drumm et al. |
| 2014/0036203 A1 | 2/2014 | Guillou et al. |
| 2014/0055421 A1 | 2/2014 | Christiansson et al. |
| 2014/0063853 A1 | 3/2014 | Nichol et al. |
| 2014/0071653 A1 | 3/2014 | Thompson et al. |
| 2014/0085241 A1 | 3/2014 | Christiansson et al. |
| 2014/0092052 A1 | 4/2014 | Grunthaner et al. |
| 2014/0098032 A1 | 4/2014 | Ng et al. |
| 2014/0098058 A1 | 4/2014 | Baharav et al. |
| 2014/0109219 A1 | 4/2014 | Rohrweck et al. |
| 2014/0125633 A1 | 5/2014 | Fåhraeus et al. |
| 2014/0139467 A1 | 5/2014 | Ghosh et al. |
| 2014/0160762 A1 | 6/2014 | Dudik et al. |
| 2014/0192023 A1 | 7/2014 | Hoffman |
| 2014/0232669 A1 | 8/2014 | Ohlsson et al. |
| 2014/0237401 A1 | 8/2014 | Krus et al. |
| 2014/0237408 A1 | 8/2014 | Ohlsson et al. |
| 2014/0237422 A1 | 8/2014 | Ohlsson et al. |
| 2014/0253831 A1 | 9/2014 | Craven-Bartle |
| 2014/0267124 A1 | 9/2014 | Christiansson et al. |
| 2014/0292701 A1 | 10/2014 | Christiansson et al. |
| 2014/0300572 A1 | 10/2014 | Ohlsson et al. |
| 2014/0320460 A1 | 10/2014 | Johansson et al. |
| 2014/0347325 A1 | 11/2014 | Wallander et al. |
| 2014/0362046 A1 | 12/2014 | Yoshida |
| 2014/0368471 A1 | 12/2014 | Christiansson et al. |
| 2014/0375607 A1 | 12/2014 | Christiansson et al. |
| 2015/0002386 A1 | 1/2015 | Mankowski et al. |
| 2015/0015497 A1 | 1/2015 | Leigh |
| 2015/0035774 A1 | 2/2015 | Christiansson et al. |
| 2015/0035803 A1 | 2/2015 | Wassvik et al. |
| 2015/0053850 A1 | 2/2015 | Uvnäs |
| 2015/0054759 A1 | 2/2015 | Christiansson et al. |
| 2015/0083891 A1 | 3/2015 | Wallander |
| 2015/0103013 A9 | 4/2015 | Huang |
| 2015/0130769 A1 | 5/2015 | Björklund |
| 2015/0138105 A1 | 5/2015 | Christiansson et al. |
| 2015/0138158 A1 | 5/2015 | Wallander et al. |
| 2015/0138161 A1 | 5/2015 | Wassvik |
| 2015/0205441 A1 | 7/2015 | Bergström et al. |
| 2015/0215450 A1 | 7/2015 | Seo et al. |
| 2015/0242055 A1 | 8/2015 | Wallander |
| 2015/0317036 A1 | 11/2015 | Johansson et al. |
| 2015/0324028 A1 | 11/2015 | Wassvik et al. |
| 2015/0331544 A1 | 11/2015 | Bergström et al. |
| 2015/0331545 A1 | 11/2015 | Wassvik et al. |
| 2015/0331546 A1 | 11/2015 | Craven-Bartle et al. |
| 2015/0331547 A1 | 11/2015 | Wassvik et al. |
| 2015/0332655 A1 | 11/2015 | Krus et al. |
| 2015/0346856 A1 | 12/2015 | Wassvik |
| 2015/0346911 A1 | 12/2015 | Christiansson |
| 2015/0363042 A1 | 12/2015 | Krus et al. |
| 2016/0026337 A1 | 1/2016 | Wassvik et al. |
| 2016/0034099 A1 | 2/2016 | Christiansson et al. |
| 2016/0050746 A1 | 2/2016 | Wassvik et al. |
| 2016/0070415 A1 | 3/2016 | Christiansson et al. |
| 2016/0070416 A1 | 3/2016 | Wassvik |
| 2016/0124546 A1 | 5/2016 | Chen et al. |
| 2016/0124551 A1 | 5/2016 | Christiansson et al. |
| 2016/0154531 A1 | 6/2016 | Wall |
| 2016/0154532 A1 | 6/2016 | Campbell |
| 2016/0202841 A1 | 7/2016 | Christiansson et al. |
| 2016/0216844 A1 | 7/2016 | Bergström |
| 2016/0224144 A1 | 8/2016 | Klinghult et al. |
| 2016/0299593 A1 | 10/2016 | Christiansson et al. |
| 2016/0328090 A1 | 11/2016 | Klinghult |
| 2016/0328091 A1 | 11/2016 | Wassvik et al. |
| 2016/0334942 A1 | 11/2016 | Wassvik |
| 2016/0342282 A1 | 11/2016 | Wassvik |
| 2016/0357348 A1 | 12/2016 | Wallander |
| 2017/0010688 A1 | 1/2017 | Fahraeus et al. |
| 2017/0090090 A1 | 3/2017 | Craven-Bartle et al. |
| 2017/0102827 A1 | 4/2017 | Christiansson et al. |
| 2017/0115235 A1 | 4/2017 | Ohlsson et al. |
| 2017/0139541 A1 | 5/2017 | Christiansson et al. |
| 2017/0177163 A1 | 6/2017 | Wallander et al. |
| 2017/0185230 A1 | 6/2017 | Wallander et al. |

FOREIGN PATENT DOCUMENTS

| | | |
|---|---|---|
| CN | 201437963 U | 4/2010 |
| CN | 101019071 B | 6/2012 |
| CN | 101206550 B | 6/2012 |
| CN | 101075168 B | 4/2014 |
| DE | 3511330 C2 | 5/1988 |
| DE | 68902419 T2 | 3/1993 |
| DE | 69000920 T2 | 6/1993 |
| DE | 19809934 A1 | 9/1999 |
| DE | 10026201 A1 | 12/2000 |
| DE | 102010000473 A1 | 8/2010 |
| EP | 0845812 B1 | 6/1998 |
| EP | 0600576 B1 | 10/1998 |
| EP | 1798630 A2 | 6/2007 |
| EP | 0897161 B1 | 10/2007 |
| EP | 2088501 A1 | 8/2009 |
| EP | 1512989 B1 | 9/2009 |
| EP | 2077490 A3 | 1/2010 |
| EP | 1126236 B1 | 12/2010 |
| EP | 2314203 A1 | 4/2011 |
| EP | 2339437 A3 | 10/2011 |
| EP | 2442180 A1 | 4/2012 |
| EP | 2466429 A1 | 6/2012 |
| EP | 2479642 A1 | 7/2012 |
| EP | 1457870 B1 | 8/2012 |
| FR | 2172828 A1 | 10/1973 |
| FR | 2617619 B1 | 1/1990 |
| FR | 2614711 B1 | 3/1992 |
| FR | 2617620 B1 | 9/1992 |
| FR | 2676275 A1 | 11/1992 |
| GB | 1380144 A | 1/1975 |
| GB | 2131544 B | 3/1986 |
| GB | 2204126 A | 11/1988 |
| JP | 2000506655 A | 5/2000 |
| JP | 2000172438 A | 6/2000 |
| JP | 2000259334 A | 9/2000 |
| JP | 2000293311 A | 10/2000 |
| JP | 2003330603 A | 11/2003 |
| JP | 2005004278 A | 1/2005 |
| JP | 2008506173 A | 2/2008 |
| JP | 2011530124 A | 12/2011 |
| KR | 100359400 | 7/2001 |
| KR | 100940435 | 2/2010 |

(56) References Cited

FOREIGN PATENT DOCUMENTS

| | | |
|---|---|---|
| WO | WO 1984/003186 A1 | 8/1984 |
| WO | WO 1999/046602 A1 | 9/1999 |
| WO | WO 0127867 A1 | 4/2001 |
| WO | WO 01/84251 A2 | 11/2001 |
| WO | WO 02/35460 A1 | 5/2002 |
| WO | WO 02/077915 A2 | 10/2002 |
| WO | WO 02/095668 A1 | 11/2002 |
| WO | WO 03/076870 A1 | 9/2003 |
| WO | WO 2004/081502 A2 | 9/2004 |
| WO | WO 2004/081956 A2 | 9/2004 |
| WO | WO 2005/026938 A2 | 3/2005 |
| WO | WO 2005/029172 A2 | 3/2005 |
| WO | WO 2005/029395 A2 | 3/2005 |
| WO | WO 2005/125011 A1 | 12/2005 |
| WO | WO 2006/095320 A2 | 9/2006 |
| WO | WO 2006/124551 A2 | 11/2006 |
| WO | WO 2007/003196 A2 | 1/2007 |
| WO | WO 2007/058924 A2 | 5/2007 |
| WO | WO 2007/112742 A1 | 10/2007 |
| WO | WO 2008/004103 A2 | 1/2008 |
| WO | WO 2008/007276 A2 | 1/2008 |
| WO | WO 2008/017077 A2 | 2/2008 |
| WO | WO 2008/039006 A1 | 4/2008 |
| WO | WO 2008/068607 A2 | 6/2008 |
| WO | WO 2006/124551 B1 | 7/2008 |
| WO | WO 2008/017077 A4 | 2/2009 |
| WO | WO 2009/048365 A1 | 4/2009 |
| WO | WO 2009/077962 A2 | 6/2009 |
| WO | WO 2009/102681 A2 | 8/2009 |
| WO | WO 2009/137355 A2 | 11/2009 |
| WO | WO 2010/006882 A2 | 1/2010 |
| WO | WO 2010/006883 A2 | 1/2010 |
| WO | WO 2010/006884 A2 | 1/2010 |
| WO | WO 2010/006885 A2 | 1/2010 |
| WO | WO 2010/006886 A2 | 1/2010 |
| WO | WO 2010/015408 A1 | 2/2010 |
| WO | WO 2010/046539 A1 | 4/2010 |
| WO | WO 2010/056177 A1 | 5/2010 |
| WO | WO 2010/064983 A2 | 6/2010 |
| WO | WO 2010/081702 A2 | 7/2010 |
| WO | WO 2010/112404 A1 | 10/2010 |
| WO | WO 2010/123809 A2 | 10/2010 |
| WO | WO 2010/134865 A1 | 11/2010 |
| WO | WO 2011/028169 A1 | 3/2011 |
| WO | WO 2011/028170 A1 | 3/2011 |
| WO | WO 2011/049511 A1 | 4/2011 |
| WO | WO 2011/049513 A1 | 4/2011 |
| WO | WO 2011049512 A1 | 4/2011 |
| WO | WO 2011/057572 A1 | 5/2011 |
| WO | WO 2011/078769 A1 | 6/2011 |
| WO | WO 2011/082477 A1 | 7/2011 |
| WO | WO 2011/139213 A1 | 11/2011 |
| WO | WO 2012/002894 A1 | 1/2012 |
| WO | WO 2012/010078 A1 | 1/2012 |
| WO | WO 2012/050510 A1 | 4/2012 |
| WO | WO 2012/082055 A1 | 6/2012 |
| WO | WO 2012/105893 A1 | 8/2012 |
| WO | WO 2012/121652 A1 | 9/2012 |
| WO | WO 2012/158105 A2 | 11/2012 |
| WO | WO 2012/172302 A1 | 12/2012 |
| WO | WO 2012/176801 A1 | 12/2012 |
| WO | WO 2013/036192 A1 | 3/2013 |
| WO | WO 2013/048312 A2 | 4/2013 |
| WO | WO 2013/055282 A2 | 4/2013 |
| WO | WO 2013/062471 A2 | 5/2013 |
| WO | WO 2013/089622 A2 | 6/2013 |
| WO | WO 2013/133756 A1 | 9/2013 |
| WO | WO 2013/133757 A2 | 9/2013 |
| WO | WO 2013/176613 A2 | 11/2013 |
| WO | WO 2013/176614 A2 | 11/2013 |
| WO | WO 2013/176615 A2 | 11/2013 |
| WO | WO 2014/055809 A1 | 4/2014 |

OTHER PUBLICATIONS

Chou, N., et al., "Generalized pseudo-polar Fourier grids and applications in regfersting optical coherence tomography images," 43rd Asilomar Conference on Signals, Systems and Computers, Nov. 2009, in 5 pages.
Fihn, M., "Touch Panel—Special Edition," Veritas et Visus, Nov. 2011, in 1 page.
Fourmont, K., "Non-Equispaced Fast Fourier Transforms with Applications to Tomography," Journal of Fourier Analysis and Applications, vol. 9, Issue 5, 2003, in 20 pages.
Iizuka, K., "Boundaries, Near-Field Optics, and Near-Field Imaging," Elements of Photonics, vol. 1: In Free Space and Special Media, Wiley & Sons, 2002, in 57 pages.
Johnson, M., "Enhanced Optical Touch Input Panel", IBM Technical Discolusre Bulletin, 1985, in 3 pages.
Kak, et al., "Principles of Computerized Tomographic Imaging", Institute of Electrical Engineers, Inc., 1999, in 333 pages.
The Laser Wall, MIT, 1997, http://web.media.mit.edu/~joep/SpectrumWeb/captions/Laser.html.
Liu, J., et al. "Multiple touch points identifying method, involves starting touch screen, driving specific emission tube, and computing and transmitting coordinate of touch points to computer system by direct lines through interface of touch screen," 2007, in 25 pages.
Natterer, F., "The Mathematics of Computerized Tomography", Society for Industrial and Applied Mathematics, 2001, in 240 pages.
Natterer, F., et al. "Fourier Reconstruction," Mathematical Methods in Image Reconstruction, Society for Industrial and Applied Mathematics, 2001, in 12 pages.
Paradiso, J.A., "Several Sensor Approaches that Retrofit Large Surfaces for Interactivity," ACM Ubicomp 2002 Workshop on Collaboration with Interactive Walls and Tables, 2002, in 8 pages.
Tedaldi, M., et al. "Refractive index mapping of layered samples using optical coherence refractometry," Proceedings of SPIE, vol. 7171, 2009, in 8 pages.

* cited by examiner

DETECTION OF SURFACE CONTAMINATION

CROSS-REFERENCE TO RELATED APPLICATIONS

This application claims the benefit and priority to and is a U.S. National Phase of PCT International Application Number PCT/SE2015/050724, filed on Jun. 22, 2015. This application claims the benefit and priority to Swedish patent application No. 1450796-6, filed 27 Jun. 2014. The disclosure of the above-referenced applications are hereby expressly incorporated by reference in their entirety.

TECHNICAL FIELD

The present invention relates to contamination sensing systems and data processing techniques in relation to such systems.

BACKGROUND

Contamination of glass surfaces by water, grease, dirt, dust, or any other substance, can be a problem in a range of circumstances. In applications such as windows or vehicle windscreens, it is important to maintain excellent optical clarity through the glass panel. In the example of the vehicle windscreen, contamination such as rain or dirt on a windscreen panel can obscure the driver's view and create a driving hazard. There is a need to detect the presence of contamination and provide a response mechanism, such as activating the use of windscreen washer fluid and windscreen wipers. US20070096015 A1 describes the use of FTIR (frustrated total internal reflection) to determine the presence of rain on the surface of a vehicle windscreen by directing a beam of light into the glass windscreen. When the windscreen is clean, the beam of light is totally internally reflected and received by a sensor. When the windscreen is wet, the light is absorbed by the water and the total internal reflection is frustrated. The change in the reflective properties of the glass can be detected in order to determine the presence of rain on the glass.

Other examples of glass (or simply transparent) panels that might benefit from a means for detecting the presence of contamination may include shop windows or museum displays, where the need for optical clarity is high, while the risk of contamination from human hands is also high. Human fingers usually deposit grease on the surface of any object they touch and, over time, the build-up of grease can result in a visible dirty effect on the touched surface.

In certain applications, the presence of surface contamination on a transparent panel may have consequences that extend beyond merely degrading the optical clarity of the panel. Touch sensitive panels, such as those used on touch sensitive displays, are known to suffer from performance degradation when the touch sensitive surface is contaminated with water, finger grease, etc. This effect can be observed particularly with projected capacitive touch technology and in-glass optical touch technologies using techniques such as scatter detection or detection of light attenuation. An example of an FTIR optical touch technology which might suffer from contamination is shown in U.S. Pat. No. 7,432,893. Further examples of touch sensitive systems operating by FTIR are disclosed in U.S. Pat. No. 8,581,884, US 2013/0044073 and US 2011/0074735. Therefore, there may be a particular need for a touch sensitive surface to detect and react to surface contamination of a touch sensitive panel.

In other applications, the presence of surface contamination may represent additional problems beyond those of optical performance or touch performance. In the field of medical instruments, it may be critical that certain surfaces remain free of contamination which may host infectious agents. The use of a touch display in an operating theatre, for example, may allow surgeons to access vital information during a surgical operation. However, if the touch display becomes contaminated with fluids or dirt during the operation, it might be critical that the display is able to detect and react to the contamination.

Therefore, there is a need for an accurate and fast method of determining contamination of a transparent panel which can provide contamination information across a contamination sensitive area.

SUMMARY

A first aspect of the invention describes a surface contamination sensing apparatus, comprising: a light transmissive element that defines a surface; a set of emitters arranged to emit beams of light into the light transmissive element, wherein the beams of light propagate inside the light transmissive element while illuminating the surface such that an object or surface contamination on the surface causes an attenuation of the propagating light, a set of light detectors arranged proximal to the surface to receive light from the set of emitters on a plurality of light paths, a processing element configured to: determine, based on output signals from the light detectors, a transmission value for each light path; generate a transmission variance value in dependence on a comparison between transmission values of a first subset of light paths of a superset of light paths and transmission values of a second subset of light paths of the superset of light paths, determine a surface contamination on the surface in a region defined by the first and second subsets of light paths in dependence on the transmission variance value.

The transmission variance may be generated in dependence on a comparison of a lowest transmission value of the first subset of light paths and a highest transmission value of the second subset of light paths. This allows the highest ratio possible to be generated and can increase the sensitivity of the system when the quantity of contamination is low. Alternatively, the transmission variance value may be generated in dependence on a comparison of an average value of the transmission values of the first subset of light paths and an average value of the transmission values of the second subset of light paths. This variation is less susceptible to noise but provides less sensitivity to contamination.

Preferably, the first and second subsets of light paths comprise light paths with an angle within 40 degrees of any other member of their respective set. The first and second subsets of light paths may comprise light paths having a length with a maximum variance of 10% from the length of any other member of their respective set. The first subset of light paths may comprise light paths originating from the same emitter. Also, the second subset of light paths may comprise light paths originating from the same emitter. This ensures that the light paths of a set which are compared are all of a similar length and should have a similar transmission value when the panel is clean. This increases sensitivity to contamination of the panel. Preferably, the average length of light paths of first subset is longer than average length of light paths of second subset. This increases the difference between the highest and lowest transmission value.

Preferably, the surface contamination is determined in dependence on a comparison of the transmission variance value with a predetermined threshold. This allows a threshold to be selected such that if the transmission variance value exceeds the value, an action may be taken by the system (e.g. notify the user of the contamination).

In one embodiment, each of the first and second subset of light paths each comprise a single light path and wherein the transmission variance value is a ratio between the transmission value of the light path of the first subset and a transmission value of the light path of the second subset. This arrangement allows the comparison of individual light paths within the superset, leading to a potentially more regionally focused contamination detection. The light path of the first subset may be the light path of the superset of light paths with the lowest transmission value and light path of the second subset may be the light path of the superset of light paths with the highest transmission value. This allows the highest ratio possible to be generated and can increase the sensitivity of the system when the quantity of contamination is low. In this embodiment, the superset of light paths may be configured to comprise light paths with an angle within 40 degrees of any other member of the superset and may be configured to have a length with a maximum variance of 10% from the length of any other member of the superset. Preferably, the superset of light paths comprises light paths originating from the same emitter.

The processing element may be further configured to: generate a plurality of transmission variance values for a plurality of supersets of light paths, and determine a surface contamination on the surface (1) in a region defined by the plurality of supersets of light paths in dependence on the average of the plurality of transmission variance values. This can provide a determination of a global contamination of the panel. Alternatively, the processing element may be further configured to: generate a plurality of transmission variance values for a plurality of supersets of light paths, and determine, from the plurality of transmission variance values, a map of a surface contamination on at least a portion of the surface. The map of the surface contamination on at least a portion of the surface may be generated by means of a back-projection of the plurality of transmission variance values onto the map. This can provide a regional determination of the panel.

A second aspect describes a method in a contamination detecting apparatus, said contamination detecting apparatus comprising: a light transmissive element that defines a surface; a set of emitters arranged to emit beams of light into the light transmissive element, wherein the beams of light propagate inside the light transmissive element while illuminating the surface such that an object or surface contamination on the surface causes an attenuation of the propagating light, and a set of light detectors arranged proximal to the surface to receive light from the set of emitters on a plurality of light paths: said method comprising the steps of: determining, based on output signals of the light detectors, a transmission value for each light path; generating a transmission variance value in dependence on a comparison between transmission values of a first subset of light paths of a superset of light paths and transmission values of a second subset of light paths of the superset of light paths, determining a surface contamination on the surface in a region defined by the first and second subsets of light paths in dependence on the transmission variance value.

A third aspect describes a computer-readable medium storing processing instructions that, when executed by a processor, performs the method of the second aspect.

BRIEF DESCRIPTION OF DRAWINGS

Embodiments of the invention will now be described in more detail with reference to the accompanying schematic drawings.

DETAILED DESCRIPTION OF EXAMPLE EMBODIMENTS

Figure 1A:
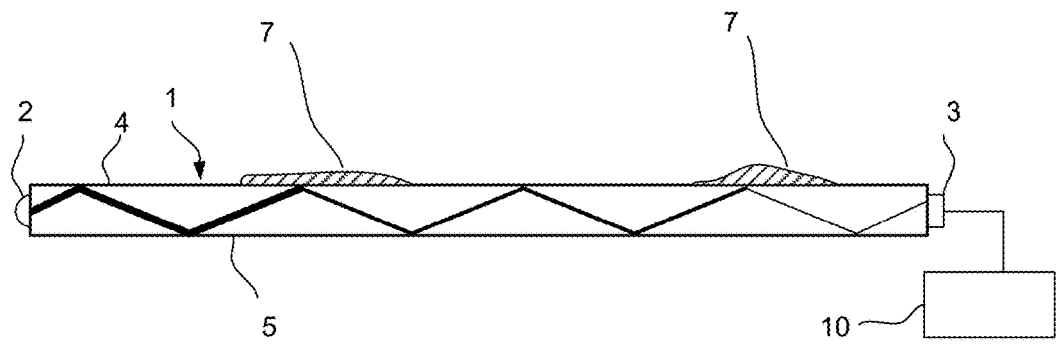
FIGS. 1a-1b are section and top plan views of an FTIR-based system of projection-type.

Throughout the following description, the same reference numerals are used to identify corresponding elements.

Panel

Figure 1B:
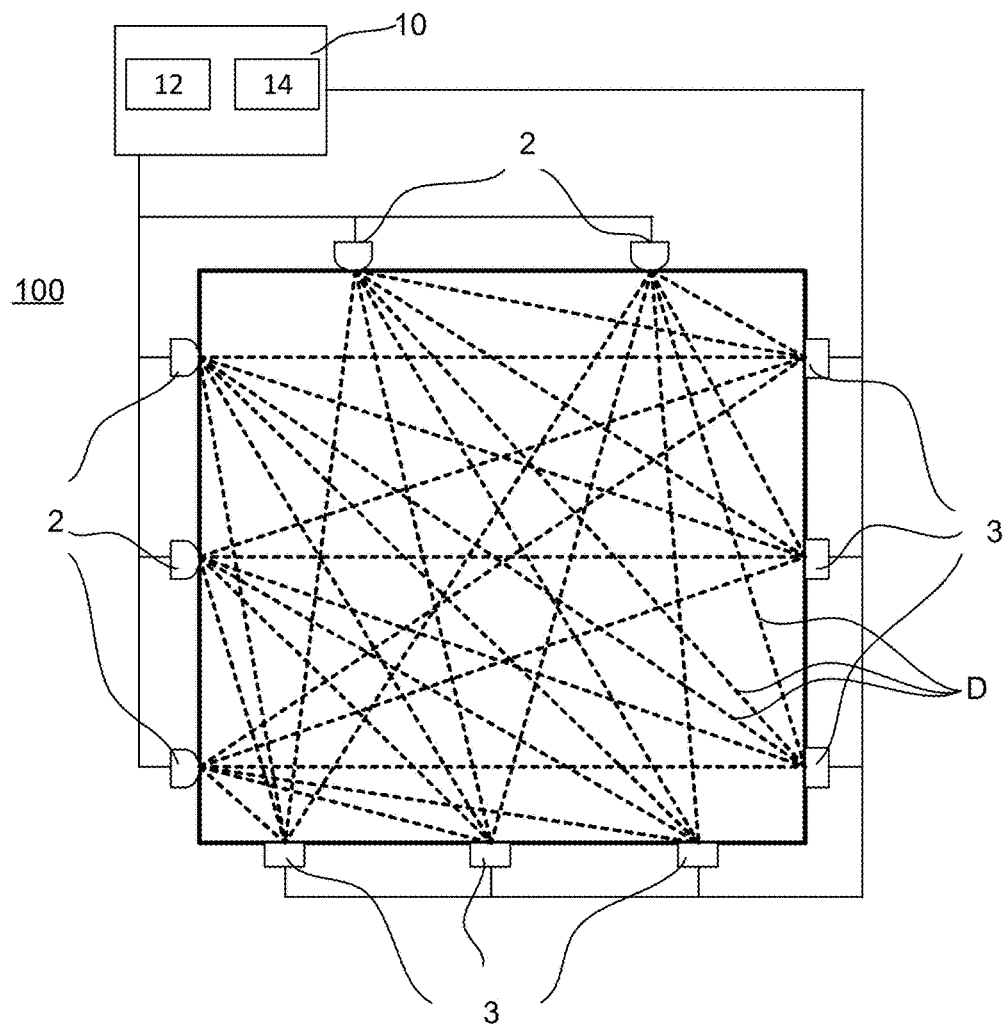

FIGS. 1A-1B illustrate an example embodiment of a surface contamination detection apparatus 100 that is based on the concept of FTIR (Frustrated Total Internal Reflection), also denoted "FTIR system". The apparatus operates by transmitting light inside a panel 1, from light emitters 2 to light sensors or detectors 3, so as to illuminate a surface 4 from within the panel 1. The panel 1 is made of solid material in one or more layers and may have any shape. The panel 1 defines an internal radiation propagation channel, in which light propagates by internal reflections. In the example of FIG. 1, the propagation channel is defined between the boundary surfaces 4, 5 of the panel 1, where the top surface 4 allows the propagating light to interact with contamination 7. This is achieved by injecting the light into the panel 1 such that the light is reflected by total internal reflection (TIR) in the surface 4 as it propagates through the panel 1. The light may be reflected by TIR in the bottom surface 5 or against a reflective coating thereon. It is also conceivable that the propagation channel is spaced from the bottom surface 5, e.g. if the panel comprises multiple layers of different materials.

Attenuation

The apparatus 100 allows surface contamination 7 that is in contact with the surface 4 to interact with the propagating light. In this interaction, part of the light may be scattered by the surface contamination 7, part of the light may be absorbed by the surface contamination 7, and part of the light may continue to propagate in its original direction across the panel 1. Thus, the surface contamination 7 causes a local frustration of the total internal reflection, which leads to a decrease in the energy (power/intensity) of the transmitted light, as indicated by the thinned lines downstream of the surface contamination 7 in FIG. 1A.

Emitters

The emitters 2 are distributed along the perimeter of the surface 4 to generate a corresponding number of light sheets inside the panel 1. In the example of FIG. 1B, each emitter 2 generates a beam of light that expands in the plane of the panel 1 while propagating in the panel 1. Each beam propagates from one or more entry or incoupling points on the panel 1.

Detectors

The sensors 3 are distributed along the perimeter of the surface 4 to receive the light from the emitters 2 at a number of spaced-apart outcoupling points on the panel 1. It should be understood that the incoupling and outcoupling points merely refer to the position where the beam enters and leaves, respectively, the panel 1. Thus, one emitter/sensor may be optically coupled to a number of incoupling/outcoupling points. As used herein, a "detection line" is defined as the line extending from one incoupling point to one outcoupling point. In the example of FIG. 1B, however, the detection lines D are defined by individual emitter-sensor pairs.

Signal Processor

The sensors 3 collectively provide an output signal, which is received and sampled by a signal processor 10. The output signal contains a number of sub-signals, also denoted "projection signals", each representing the energy of light emitted by a certain light emitter 2 and received by a certain light sensor 3. The signal processor 10 may need to process the output signal for separation of the individual projection signals. Conceptually, the apparatus 100 is considered to define a grid of detection lines D on the surface 4, where each detection line D corresponds to a light propagation path from an emitter 2 to a sensor 3, as projected onto the surface 4. Thus, the projection signals represent the received energy or power of light on the individual detection lines D. It is realized that the surface contamination 7 results in a decrease (attenuation) of the received energy on one or more detection lines D.

As will be explained below, the signal processor 10 may be configured to process the projection signals to provide transmission values which may then be used to determine one or more variances in the attenuation of the individual signals. The variances can then be processed according to the algorithms of the present invention to determine a surface contamination of the panel surface 4.

Controller

In the illustrated example, the apparatus 100 also includes a controller 12 which is connected to selectively control the activation of the emitters 2 and, possibly, the readout of data from the sensors 3. The signal processor 10 and the controller 12 may be configured as separate units, or they may be incorporated in a single unit. One or both of the signal processor 10 and the controller 12 may be at least partially implemented by software executed by a processing unit 14.

Similar Sequence Methods

It is to be understood that FIGS. 1*a* and 1*b* merely illustrates one example of an FTIR system. For example, the detection lines may instead be generated by sweeping or scanning one or more beams of light inside the panel 1, and the light may instead be coupled into and out of the panel 1 via the top and bottom surfaces 4, 5, e.g. by the use of dedicated coupling elements attached to the panel 1. Prior art documents disclosing alternative FTIR systems are listed in the Background section, all of which are incorporated herein by this reference. The inventive concept may be applied to such alternative FTIR systems as well.

Data Extraction Process

Figure 2:
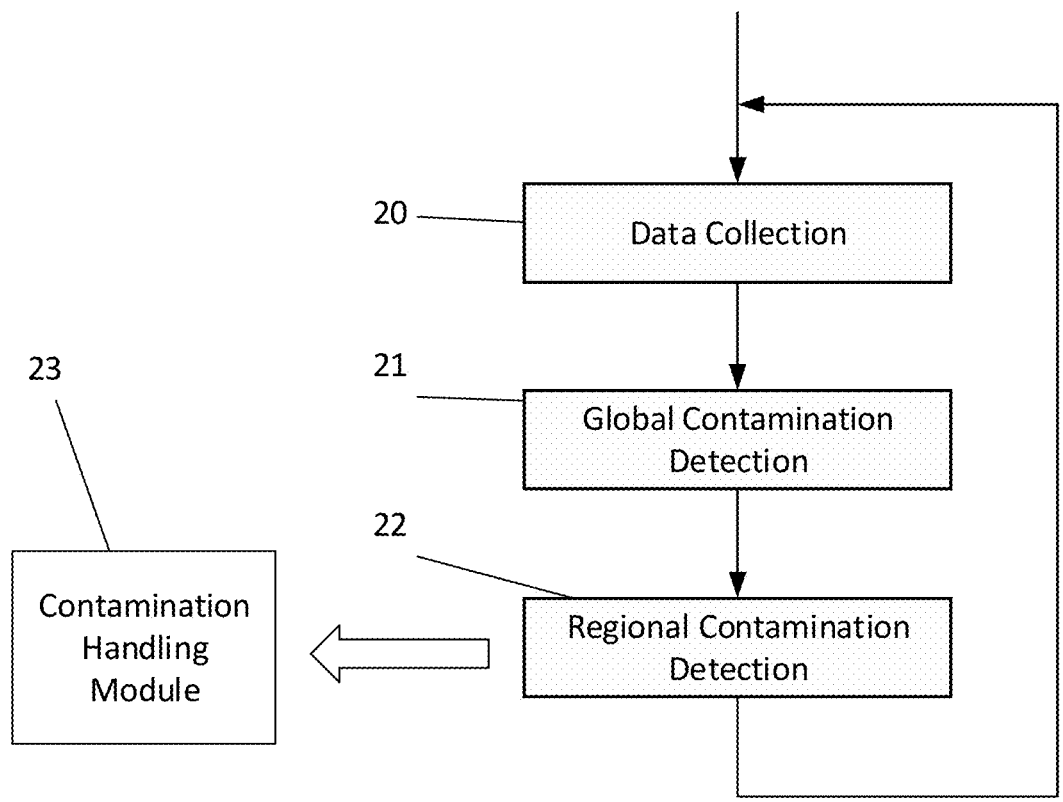
FIG. 2 is a flowchart of a data extraction process in the system of FIG. 1.

FIG. 2 is a flow chart of a contamination detection process in an FTIR system. The process involves a sequence of steps 20-23 that are repeatedly executed, e.g. by the signal processor 10 (FIG. 1). In the context of this description, each sequence of steps 20-23 is denoted a frame or an iteration.

Each frame starts by a data collection step 20, in which measurement values are obtained from the light sensors 3 in the FTIR system, typically by sampling a value from each of the aforesaid projection signals. The data collection step 20 results in one transmission value for each detection line. It may be noted that the data may, but need not, be collected for all available detection lines in the FTIR system. The data collection step 20 may also include pre-processing of the measurement values, e.g. filtering for noise reduction, normalisation with a respective reference value, applying a logarithm on each measurement value.

In step 21, a determination of a global contamination on the surface of panel 1 of the FTIR system is performed according to the methods described below. In step 22, a determination of the regional contamination of the surface of panel 1 of the FTIR system is performed according to the methods described below. In step 23, the contamination handling module receives the measured global and regional contamination values and operates to perform a response e.g. notify the user of a detected contamination.

In other embodiments, global contamination detection or regional contamination detection may be performed on its own, i.e. either step 21 or step 22 would be omitted. In another embodiment, step 21 and step 22 are reversed.

Surface Contamination Detection Algorithm

Below are described two methods of determining contamination on the surface of the panel.

Global Contamination Determination

Figure 3:
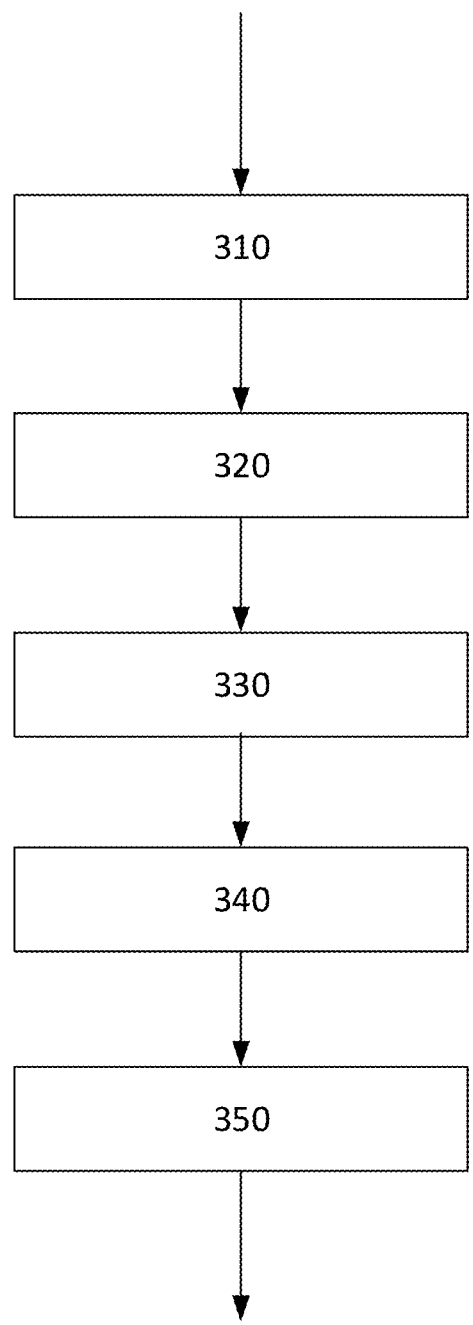
FIG. 3 is a flowchart of a global contamination detection process.

FIG. 3 is a flow chart of a global contamination detection process in an FTIR system. The process involves a sequence of steps 310-350 that are executed each time a determination of global contamination on the panel is required. In this case, a measure of the global contamination is defined as a single measure indicating the amount of contamination covering the surface. This can therefore be used to indicate total contamination regardless of whether the contamination is localized or is spread across the entire surface of the panel. An example of contamination covering the entire surface may be dust and grime collected over a long period of time, fine water droplets dispersed across the panel from rain or other sources, etc.

To determine a value of the total contamination level on the panel, two techniques are presented. These two techniques may be used individually or independently to determine a global contamination level or may be combined to produce a more accurate value of the global contamination level.

The first technique makes use of the fact that, on average, long detection lines will pass through more contamination than short ones. Consequently, longer detection lines are likely to be more attenuated than short ones. All detection lines suffer from a degree of attenuation due to 'bulk absorption' i.e. absorption of the light by the glass itself. However, for a clean panel, the transmission value for a long detection line will be only slightly less than the corresponding transmission value for a short detection line. However, for a contaminated panel, the difference between the transmission value for the long detection line and the transmission value for the short detection line will increase. For a heavily contaminated panel, the difference between the transmission values is significant. Consequently, a measure of the differences in transmission values between long and short detection lines can provide a determination of the contamination in the areas crossed by the detection lines. This technique gives particularly good estimation of attenuation of the panel when the panel is uniformly contaminated.

Figure 4A:
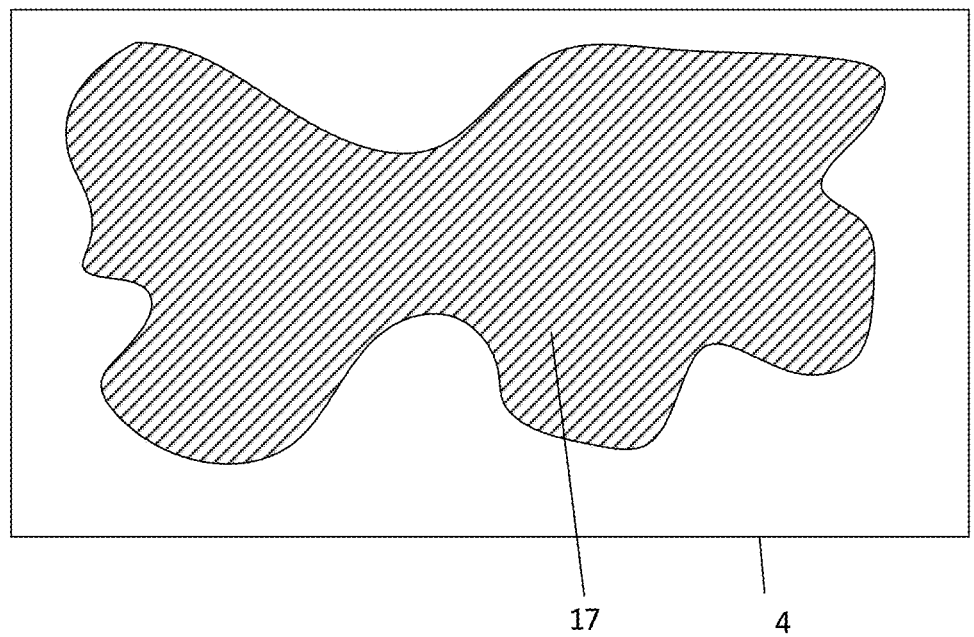
FIG. 4a-4b illustrate a globally contaminated panel and the detection lines used to detect the global contamination.

The second technique makes use of the fact that contamination is rarely completely uniform. The transmission values are compared for a set of detection lines that have approximately the same transmission value when the panel is clean. By determining a ratio between strongest and weakest transmission values of the compared detection lines, a determination of contamination of the panel can be made. i.e. The variation between the strongest and weakest detection lines (i.e. the detection lines with the strongest and weakest transmission values) increases as the contamination has a random effect on the attenuation of the detection lines. The strongest line from this subset will be the detection line that goes through the least amount of contamination and the weakest line will go through the most amount of contamination. As the ratio between the strongest and weakest transmission value rises, the probability of the presence of contamination in the region which the lines pass through is increased In a preferred embodiment, a combination of the two techniques is employed. In the preferred embodiment, the maximum transmission values for a set of short detection lines is compared to the minimum transmission values for a set of long detection lines. This combination of the presented techniques becomes even more suitable for determining the global contamination level. The maximum transmission value of a relatively large set of short detection lines is the detection line that has been attenuated by the least amount of contamination. The minimum transmission value of a relatively large set of long detection lines is the detection line that has gone through the most amount of contamination. The ratio between these two transmission values is a good indicator of the global level of contamination on the panel Implementation FIG. 4a shows a surface 4 with global contamination 17.

Figure 4B:
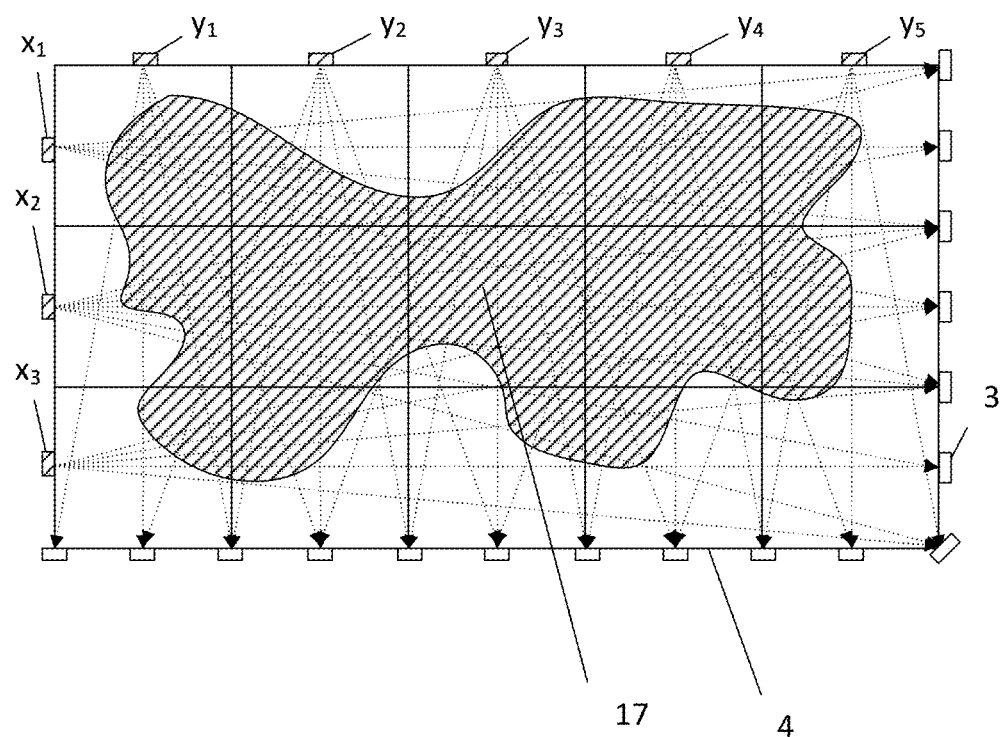

In step 310 of FIG. 3, a set of detection lines are selected for use in the contamination determination. In a preferred embodiment shown in FIG. 4b, detection lines from each emitter are used. For each of the emitters ($x_1$, $x_2$, $x_3$ ...) along the short edge, a set ($U_{x1}$, $U_{x2}$, $U_{x3}$ ...) of detection lines within ±20 degrees of the horizontal axis of the panel is selected for use with the process. i.e. $U_{x1}$ is a set of detection lines from emitter $x_1$. For each of the emitters ($y_1$, $y_2$, $y_3$ ...) along the long edge, a set ($U_{y1}$, $U_{y2}$, $U_{y3}$ ...) of detection lines within ±20 degrees of the vertical axis of the panel is selected for use with the process. i.e. $U_{y1}$ is a set of detection lines from emitter $y_1$.

In step 320, the detection line with the lowest transmission values (i.e. weakest projection signal) from each of set ($U_{x1}$, $U_{x2}$, $U_{x3}$ ...) is selected. The transmission values of the selected detection lines are summed.

In step 330, the detection line with the highest transmission values (i.e. strongest projection signals) from each of set ($U_{y1}$, $U_{y2}$, $U_{y3}$) is selected. The transmission values of the selected detection lines are summed.

In step 340, a ratio of the sum of the highest transmission values and the sum of the lowest transmission values is output as a global contamination value by the system.

$$\text{Global Contamination} = \sum_{i=1}^{n} \max(Uyi) : \sum_{i=1}^{m} \min(Uxj)$$

As can be seen, both the first and second techniques described above are employed in this embodiment. However, each of these techniques may be employed alone or independently to determine the global contamination of the panel. In one embodiment using only the first technique, the average of set ($U_{y1}$, $U_{y2}$, $U_{y3}$) is calculated and compared to the average of set ($U_{x1}$, $U_{x2}$, $U_{x3}$ ...). The result is a ratio that increases with increasing contamination level of the panel.

In an embodiment using only the second technique, either the average or maximum ratio within the subsets is used. This means that for each subset, the ratio between the strongest and weakest detection lines is calculated. All these ratios are averaged and used as a measure of the global contamination level. Alternatively, the highest ratio is determined and used as a measure of the global contamination level.

In optional step 350, the global contamination is indicated on a display to a user with an instruction to clean the contaminated panel.

Regional Contamination Determination

Figure 5:
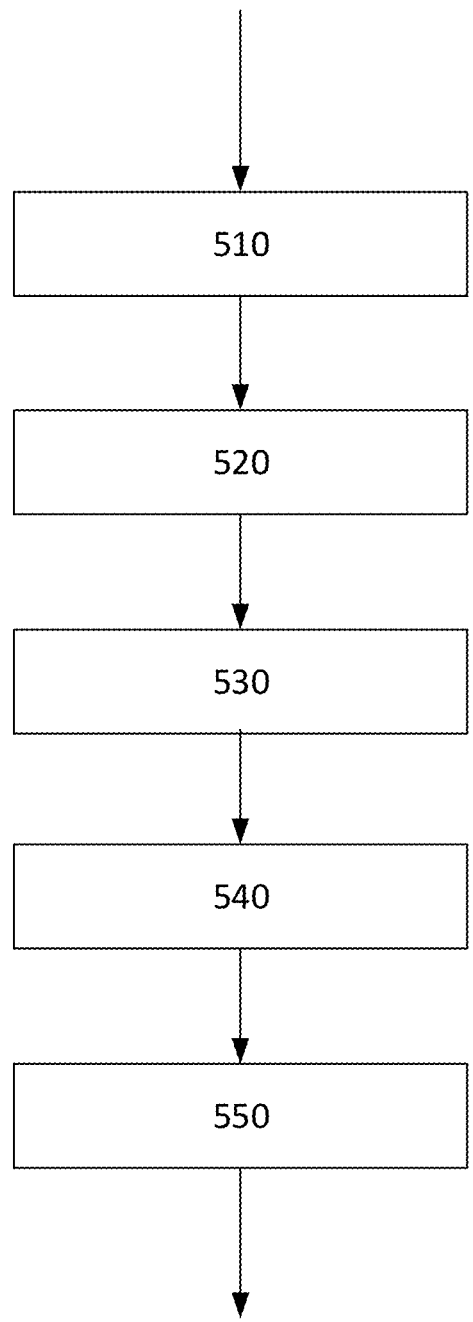
FIG. 5 is a flowchart of a regional contamination detection process.

FIG. 5 is a flow chart of a regional contamination detection process in an FTIR system. The process involves a sequence of steps 510-550 that are executed each time a determination of contamination on the panel is required which provides regional specific information about the location of the contamination.

A measure of the regional contamination is most useful when the contamination is concentrated in a small area. An example of regional contamination may be a finger smudge, a water droplet, an object resting on the surface etc.

The technique presented for regional contamination is similar to the second technique presented for global contamination determination. For a set of detection lines that have approximately the same transmission value when the panel is clean, the detection lines with the strongest and weakest transmission values respectively are determined. The ratio between the detection lines with the strongest and weakest transmission values increases as the contamination level on the panel increases. The line with the strongest transmission value from this subset will be the detection line that passes through the least amount of contamination and the detection line with the weakest transmission value will pass through the most amount of contamination.

In the technique presented for regional contamination, the ratios for a plurality of subsets of the set of detection lines are determined. Preferably, subsets each comprise detection lines from a respective emitter, i.e. each subset has detection lines from one emitter.

For each subset, the detection line most affected by contamination (i.e. the detection line with the minimum transmission value) is determined and used to determine a direction from the single emitter of the contamination affecting the detection line. This direction is determined from the known angle of the detection line from the single emitter. If the ratio determined from the subset is small, it is determined that no real indication of a regionalized contaminated area is made by the single emitter. If the ratio determined from the subset is high, probability is high of contamination in the direction indicated by the detection line with the weakest transmission value. By combining the contamination probability with the directional information from several different subsets, it becomes possible to determine a localized region on the panel that is contaminated, using techniques such as Filtered Back Projection, FFT-based algorithms, ART (Algebraic Reconstruction Technique), SART (Simultaneous Algebraic Reconstruction Technique), etc.

Implementation

Figure 6A:
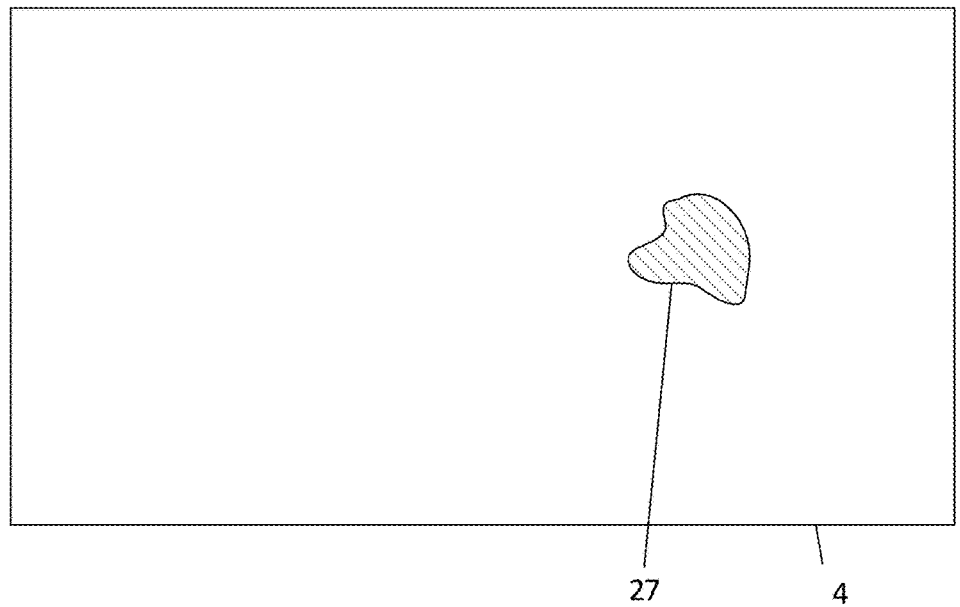
FIGS. 6a-6f a regionally contaminated panel and the detection lines used to detect the regional contamination.

FIG. 6a shows a surface 4 with regional or local contamination 27.

Figure 6B:
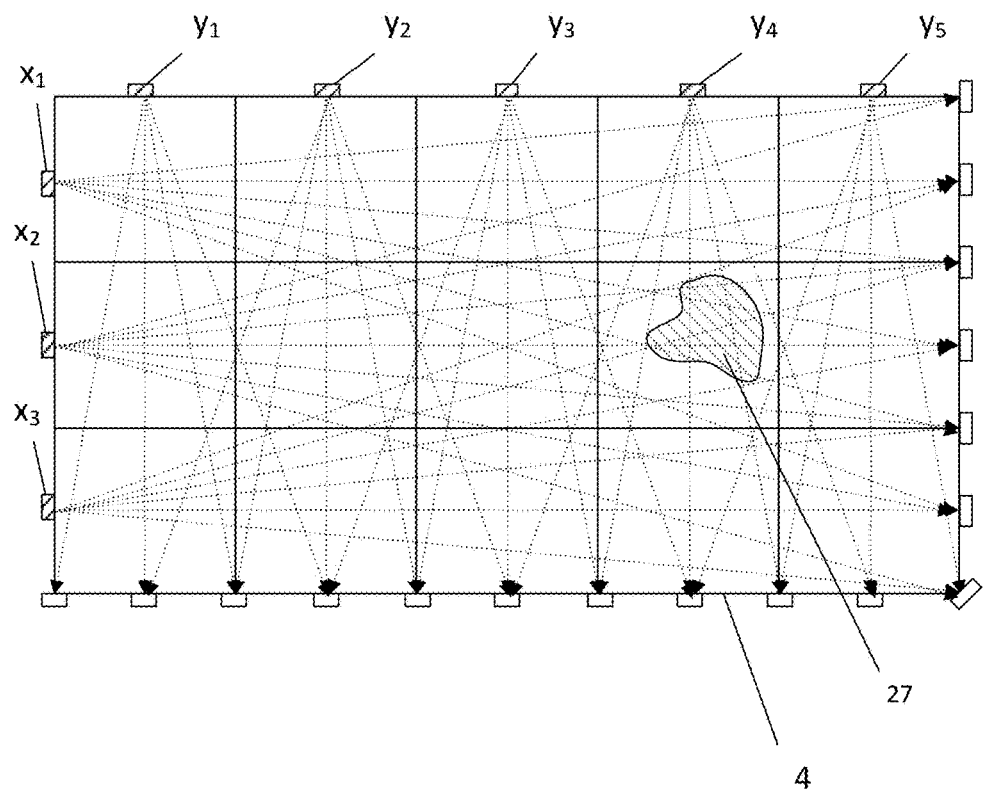

In step 510 of FIG. 5, a set of detection lines are selected for use in the contamination determination. In a preferred embodiment shown in FIG. 6b, detection lines from each emitter are used. For each of the emitters ($x_1$, $x_2$, $x_3$ . . . ) along the short edge, a set ($U_{x1}$, $U_{x2}$, $U_{x3}$ . . . ) of detection lines within ±20 degrees of the horizontal axis is selected for use with the process. For each of the emitters ($y_1$, $y_2$, $y_3$ . . . ) along the long edge, a set ($U_{y1}$, $U_{y2}$, $U_{y3}$) of detection lines within ±20 degrees of the vertical axis is selected for use with the process. It is envisaged that different angular ranges are used to determine which detection lines are included in each set. A range of between 5 degrees and 45 degrees may provide useful results.

In step 520, the detection lines with the highest and lowest transmission values from each of set $U_{x1}$, $U_{x2}$, $U_{x3}$ are compared and a ratio ($R_{x1}$, $R_{x2}$, $R_{x3}$ . . . ) between the highest and lowest transmission values is calculated for each set. Contaminated regions of the panel are likely to produce a greater variation in the transmission values of the set of detection lines traversing the contaminated region. This results in sets of detection lines with a higher ratio R value.

Figure 6C:
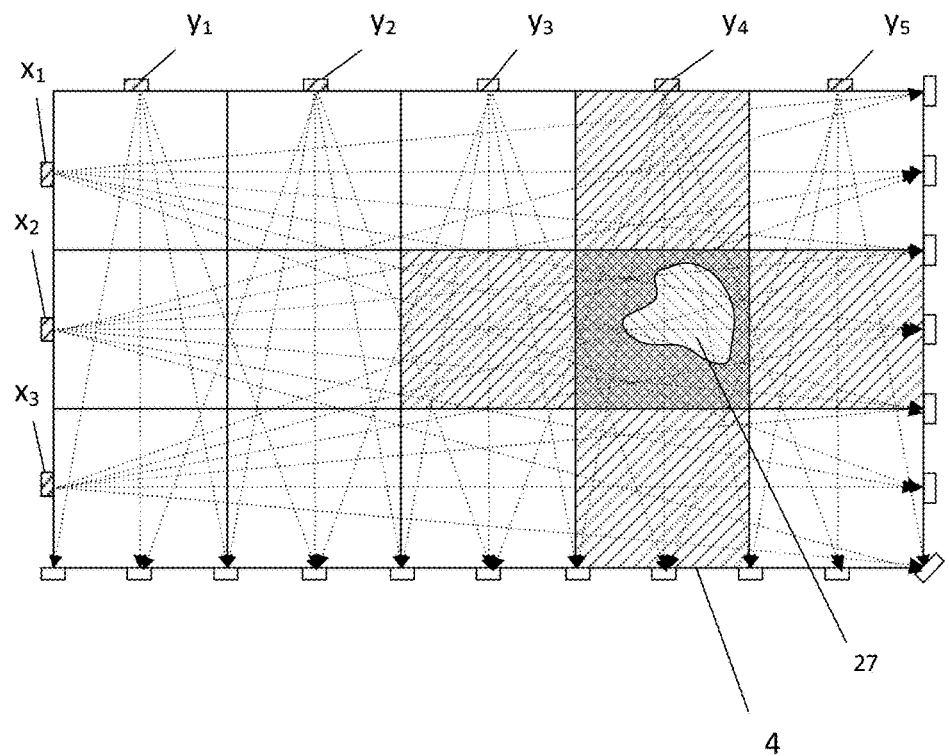

FIG. 6c shows the surface 4 divided up into a grid in dependence on the horizontally and vertically facing emitters and corresponding detection line positions. In step 530, the ratio value R for each horizontal set ($U_{x1}$, $U_{x2}$, $U_{x3}$, . . . ) and vertical set ($U_{y1}$, $U_{y2}$, $U_{y3}$, . . . ) of detection lines are back projected (described below) to the grid locations covered by at least one detection line from the set. In a preferred embodiment, the weakest detection line from each set (i.e. the detection line from the set used to calculate R with the weakest transmission value) is used to determine how each grid location is affected by the ratio value R for each set.

Figure 6D:
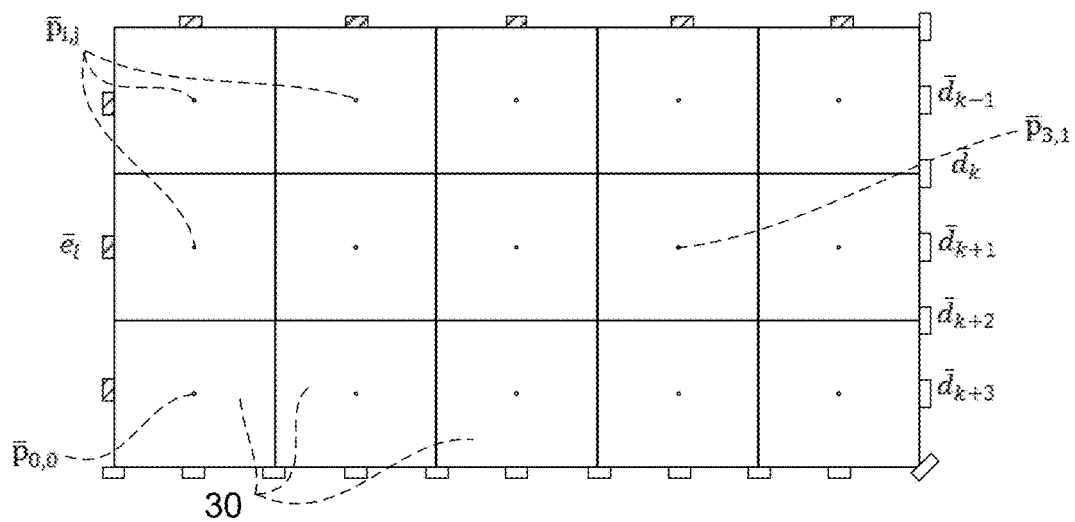

FIG. 6d shows the a map of surface 4 divided up into a grid comprising rectangular grid locations 30, each having centre point $\bar{p}_{i,j}$.

Define $\bar{p}_{i,j}=(x, y)$ to be the centre points of grid locations 30 of the map. Define $\bar{e}_l=(x, y)$ to be the positions of the emitters, $\bar{d}_k=(x, y)$ to be the positions of the detectors. The normal to the detection line given by emitter l and detector k is defined as $$\bar{n}_{kl} = \frac{\text{normal}(\bar{d}_k - \bar{e}_l)}{\|\bar{d}_k - \bar{e}_l\|_2} = \frac{(-\Delta y, \Delta x)}{\sqrt{\Delta x^2 + \Delta y^2}}.$$

Figure 6E:
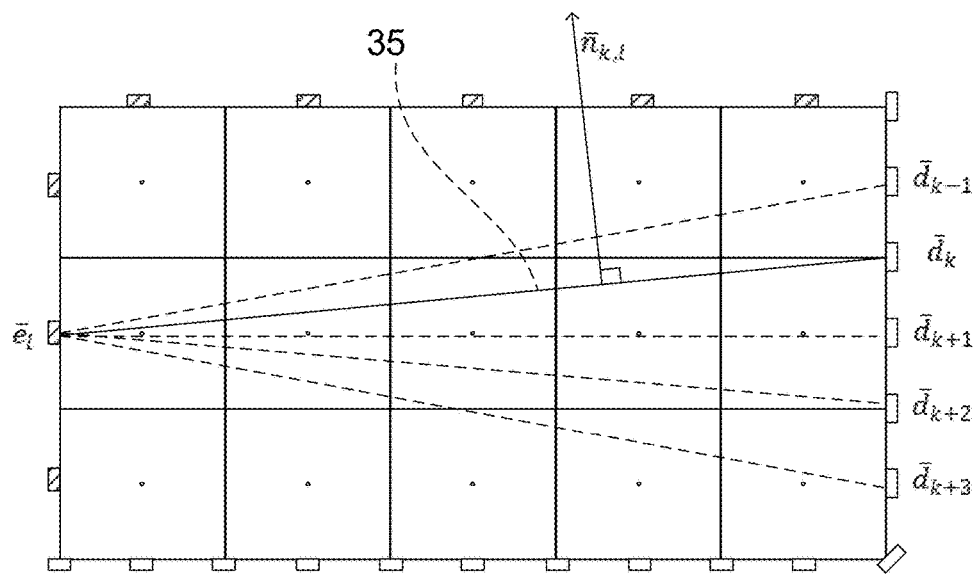

In a preferred embodiment shown in FIG. 6e, the contribution to all centre points of grid locations in the map is computed for the weakest line 35 in each set, U. For each set, U, the minimum distance between the detection line, from emitter $\bar{e}_l$ to detector $\bar{d}_k$, and all grid points (by projection onto the normal vector $\bar{n}_{k,l}$) is computed:

$$s_{i,j} = \bar{n}_{k,l} \cdot (\bar{p}_{i,j} - \bar{e}_l)$$

For each set, U, the contribution to all grid points is computed according to $$b_{i,j}^U = R_U \cdot w(s_{i,j})$$

Where $R_U$ is the ratio value calculated for the respective horizontal or vertical set and where the weight function, w, describes how much contribution a point gets depending on the distance from the detection line to the grid point. Some examples are $$w(s) = e^{-s^2/2\sigma^2}$$

$$w(s) = \begin{cases} 1 & \text{if } |s| < s_{threshold} \\ 0 & \text{if } |s| \geq s_{threshold} \end{cases}$$

$$w(s) = \begin{cases} \frac{s_{threshold} - |s|}{s_{threshold}} & \text{if } |s| < s_{threshold} \\ 0 & \text{if } |s| \geq s_{threshold} \end{cases}$$

The contributions from all sets, U, are aggregated into a single map using the contributions from all sets $$b_{i,j} = \sum_U b_{i,j}^U$$

In another embodiment, the contribution to grid location $b_{i,j}^U$ is computed according to the length of the detection line that passes that particular grid location.

In a preferred embodiment, back projection of detection line is performed on two different maps comprising the grid shown in FIG. 6c. The first map is used to calculate back-projection values using the horizontal sets ($U_{x1}$, $U_{x2}$, $U_{x3}$, . . . ) and the second map is used to calculate back-projection values using the vertical sets ($U_{y1}$, $U_{y2}$, $U_{y3}$, . . . ). This results in two maps, $b^h$ (accumulated using horizontal sets) and by (accumulated using vertical sets).

The last step combines the two maps using $$b_{i,j} = b_{i,j}^h \cdot b_{i,j}^v$$

In an alternative embodiment, other combination functions may be envisaged, such as a summing of the maps.

In step 540, the value of each grid location is compared with a threshold value to determine the presence of contamination. The grid coordinate ($x_2$, $y_4$) from FIG. 6c is determined to comprise contamination on the surface of the panel.

Figure 6F:
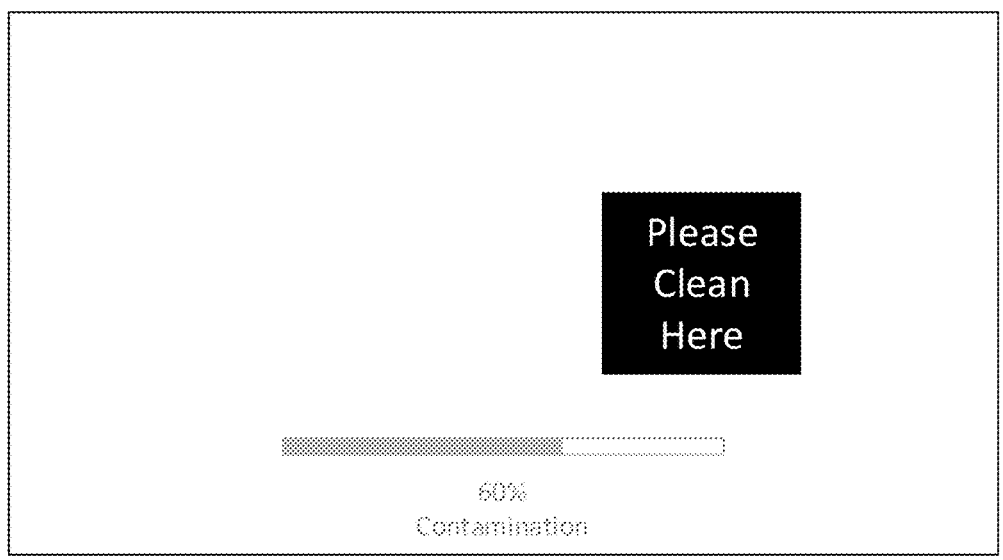

In optional step 550 shown in FIG. 6f, the contaminated region is indicated on a display to a user with an instruction to clean the contaminated region of the panel.

In an alternative embodiment of the invention, a triangulation technique is used to determine the location of contamination on the panel. First, the highest ratio from set ($R_{x1}$, $R_{x2}$, $R_{x3}$ . . . ) is determined. Then, the direction of the weakest detection line corresponding to the highest ratio from set ($R_{x1}$, $R_{x2}$, $R_{x3}$ . . . ) is determined. Similarly, the highest ratio from set ($R_{y1}$, $R_{y2}$, $R_{y3}$ . . . ) is determined. Then, the direction of the weakest detection line corresponding to the highest ratio from set ($R_{y1}$, $R_{y2}$, $R_{y3}$ . . . ) is determined. Triangulating the direction of the weakest detection line corresponding to the highest ratio from set ($R_{x1}$, $R_{x2}$, $R_{x3}$ . . . ) with the direction of the weakest detection line corresponding to the highest ratio from set ($R_{y1}$, $R_{y2}$, $R_{y3}$ . . . ) will provide an indication of the most contaminated region of the panel.

Process Execution

Figure 8:
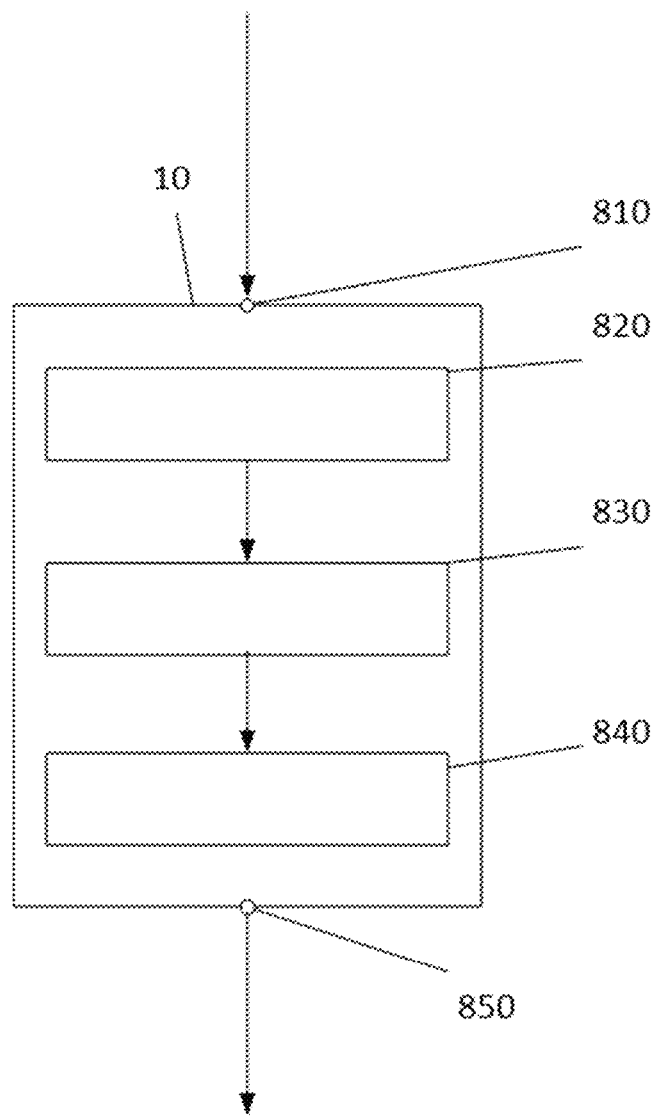
FIG. 8 shows an example of a data processing device.

The contamination determination in FIGS. 3 and 5 may be executed separately from the data collection process in FIG. 2, e.g. on separate devices or on a single device (e.g. the signal processor 10 in FIG. 1). Alternatively, the processes in FIGS. 2, 3 and 5 may be integrated into one process for execution on a single device. FIG. 8 shows an example of a data processing device 10, which includes an input 810 for receiving the projection signals. The device 10 further includes a global contamination element (or means) 820 for performing steps 310-340, a regional contamination detection element (or means) 830 for performing steps 510-550, and an output element (or means) 840 for providing global and regional contamination determination values via an output 850.

Hardware Device

The device 10 may be implemented by special-purpose software (or firmware) run on one or more general-purpose or special-purpose computing devices. In this context, it is to be understood that each "element" or "means" of such a computing device refers to a conceptual equivalent of a method step; there is not always a one-to-one correspondence between elements/means and particular pieces of hardware or software routines. One piece of hardware sometimes comprises different means/elements. For example, a processing unit may serve as one element/means when executing one instruction, but serve as another element/means when executing another instruction. In addition, one element/means may be implemented by one instruction in some cases, but by a plurality of instructions in some other cases. Naturally, it is conceivable that one or more elements (means) are implemented entirely by analogue hardware components.

The software controlled device 10 may include one or more processing units, e.g. a CPU ("Central Processing Unit"), a DSP ("Digital Signal Processor"), an ASIC ("Application-Specific Integrated Circuit"), discrete analogue and/or digital components, or some other programmable logical device, such as an FPGA ("Field Programmable Gate Array"). The device 10 may further include a system memory and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software and associated control parameter values may be stored in the system memory, or on other removable/non-removable volatile/nonvolatile computer storage media which is included in or accessible to the computing device, such as magnetic media, optical media, flash memory cards, digital tape, solid state RAM, solid state ROM, etc. The data processing device 10 may include one or more communication interfaces, such as a serial interface, a parallel interface, a USB interface, a wireless interface, a network adapter, etc, as well as one or more data acquisition devices, such as an A/D converter. The special-purpose software may be provided to the device 10 on any suitable computer-readable medium, including a record medium, and a read-only memory.

Touch Display

In one embodiment of the invention, the contamination detection function takes advantage of existing FTIR touch components such as those described in PCT publication WO2014042576 A3 "Touch force estimation in an FTIR-based projection-type touch-sensing apparatus". Where the apparatus described in WO2014042576 is used to determine contact between an object and the panel, an embodiment of the present invention uses the same apparatus for determination of surface contamination of the panel.

In a preferred embodiment, surface 4 is also a touch sensitive surface and processing element 10 is configured to determine, based on output signals of the light detectors 3, a light energy value for each light path; to generate a transmission value for each light path based on the light energy value; and to operate an image reconstruction algorithm on at least part of the thus-generated transmission values so as to determine the position of an object on the touch surface. The image reconstruction algorithm may be an algorithm for transmission tomography with a fan beam geometry.

In one embodiment, the apparatus may be configured to be switchable between a touch detection mode and a contamination detection mode. In an alternative embodiment, the contamination detection runs in parallel to the touch detection and uses the same signals recorded for touch determination. In this embodiment, the contamination detection may be executed on separate processing hardware or on the same signal processing hardware provided for touch determination.

In one embodiment, the contamination detection process runs at a lower frame rate than a touch detection process. Alternatively, the contamination detection process may be configured to collect and process only part of the contamination data in each frame. For example, contamination detection process is operated to use only emitters 1-5 from a first frame and collect the corresponding detector data, and then use only emitters 6-10 in the second frame etc. until all the emitters have been used. This method allows a reduction in the amount of processing used but leads to a slower update of the contamination mapping. However, compared with touch detection, detection of contamination is substantially less latency critical. Furthermore, there should be no changes in contamination during the time when the contamination detection process is used as it is preferably employed when there are no fingers present on the touch panel.

Although embodiments of the invention may use the same recorded signal values to determine surface contamination as those recorded to determine touch, it is important to note that the techniques for determining touch as described by the prior art are fundamentally different to the techniques described herein for determining surface contamination.

User Alerts

In one embodiment of the invention, the contamination detection apparatus is overlaid on or integrated into a display device or monitor. This may be part of an FTIR type touch system (for example, a touch display) or just a contamination detection panel for a display, e.g. for applications requiring exceptional optical clarity. Contamination handling module 23 is configured to provide alerts to a user via an operating system call, a direct software interaction, or a hardware alert e.g. via an LED, separate display, or sound alert.

Figure 7A:
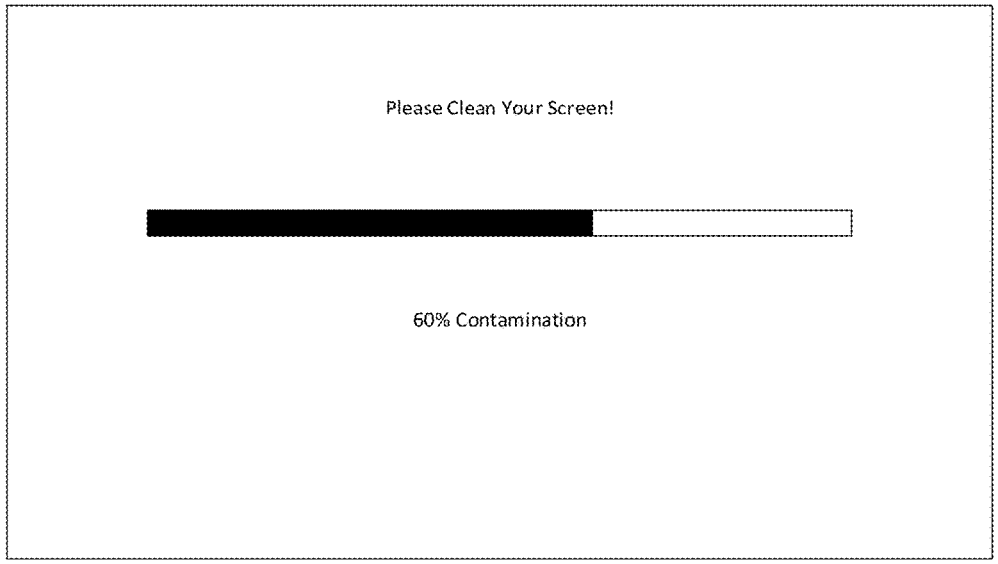
FIGS. 7a-7c show user interface configurations to alert the user to the presence, type, and location of the contamination.
Figure 7B:
Figure 7C:

FIGS. 7a-7c show embodiment of a software interface for providing contamination information to the user. In FIG. 7a, a determination of the global contamination is used to display a contamination value and corresponding 'contamination bar' to a user. The contamination value and corresponding bar are used to indicate the general level of surface contamination on the screen and provides a prompt to the user to clean the screen. In one embodiment, the contamination value is updated as the user cleans the screen, providing the user with a real time update on the effectiveness of his cleaning efforts.

In FIG. 7b, a determination of the regional contamination is used to display a region of the screen that is contaminated.

In the embodiment shown, contaminated region of the screen is marked 'clean here' as an indication to the user that the screen should be cleaned. In one embodiment, the size and position of a 'clean here' box corresponds to the position and size of the contaminated region. In an alternative embodiment, the size or colour of the box may correspond to the degree of contamination in that region. In one embodiment, the contamination value is updated as the user cleans the screen, providing the user with a real time update on the effectiveness of his or her cleaning efforts, e.g. as the indicated portion of the screen is cleaned, the size of the box may shrink to indicate less contamination. Alternatively, the colour of the box fades from a first colour (e.g. red) to a second colour (e.g. green) as the screen becomes cleaner.

In one embodiment, the 'clean here' box is repositioned from a first area to a second area of contamination once a first area of contamination has been successfully cleaned.

In an embodiment shown in FIG. 7c, a regional contamination indicator is combined with the global contamination indicator. This provides the user with an indicator of which section of the panel to focus his or her cleaning efforts, as well as an indicator of their overall progress towards a completely clean screen.

In other embodiments of the invention, the software interface is configured to provide the user with an indication of success once either the regional contamination or the global contamination has been successfully cleaned.

In another embodiment of the invention, the user interface is configured to provide an indication of the estimated loss of clarity in contaminated regions of the panel. The estimated loss of clarity may be calculated as a function of the determined regional or global contamination.

In another embodiment of the invention, the user interface is configured to provide a warning once either global or regional contamination passes a threshold. The warning may indicate the possibility and/or degree of degradation in touch performance of a touch sensitive panel. In an alternative embodiment, the warning may indicate to the user the risk of spread of infection from fluids deposited on the panel.

In another embodiment of the invention, the user interface is configured to provide an indication of the environment humidity and/or condensation affecting the panel in dependence on the global and/or regional contamination determinations.

Non-Touch Panel

In other embodiment, the contamination detection is used to determine whether contamination is present on optically critical applications, including solar panels, windows, museum displays, eye wear, and lenses of all types.

In one embodiment, contamination 7 maybe detected on both the top surface 4 and bottom surface 5 simultaneously.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. A system for detecting surface contamination on a touch screen apparatus, comprising:
   a light transmissive element that defines a surface;
   a set of emitters arranged to emit beams of light into the light transmissive element,
   wherein the beams of light propagate inside the light transmissive element while illuminating the surface such that surface contamination on the surface causes an attenuation of the propagating light,
   a set of light detectors arranged proximal to the surface to receive light from the set of emitters on a plurality of light paths, and
   a hardware processor configured to:
      determine, based on output signals from the light detectors, a transmission value for each light path in the plurality of light paths;
      determine a first group transmission value for a first plurality of light paths in the plurality of light paths, wherein the first plurality of light paths share a first property;
      determine a second group transmission value for a second plurality of lights in the plurality of light paths, wherein the second plurality of light paths share a second property different from the first property;
      generate a contamination value based on the first group transmission value with the second group transmission value; and
      display an indication of surface contamination based on the generated contamination value.

2. The system of claim 1, wherein the first group transmission value comprises a lowest transmission value of all transmission values corresponding to respective first plurality of light paths and wherein the second group transmission value comprises a highest transmission value of all transmission values corresponding to respective second plurality of light paths.

3. The system of claim 1, wherein the first group transmission value comprises an average value of all transmission values corresponding to respective first plurality of light paths and wherein the second group transmission value comprises an average value of all transmission values corresponding to respective second plurality of light paths.

4. The system of claim 1, wherein the first and second plurality of light paths comprise light paths with an angle within 40 degrees of any other member of their respective set.

5. The system of claim 1, wherein the first and second plurality of light paths comprise light paths having a length with a maximum variance of 10% from the length of any other member of their respective set.

6. The system of claim 1, wherein the first property comprises a first average length of light paths in the first plurality of light paths and the second property comprises a second average length of light paths in the second plurality of light paths, wherein the first average length is longer than the second average length.

7. The system of claim 1, wherein the first property comprises all light paths originating from the same emitter.

8. The system of claim 1, wherein the second property comprises all light paths originating from the same emitter.

9. The system of claim 1, wherein the indication of surface contamination is determined based on a comparison of the generated contamination value with a predetermined threshold.

10. The system of claim 1, wherein the first plurality of light paths are substantially perpendicular to the second plurality of light paths.

11. The system of claim 1, wherein is the contamination value is based on a ratio between the first group transmission value and the second group transmission value.

12. The system of claim 11, wherein the hardware processor is further configured to:

determine a map of a surface contamination on at least a portion of the surface.

13. The system of claim 12, wherein the map of the surface contamination on at least a portion of the surface is generated based on a back-projection of a plurality of transmission variance values onto the map.

14. A method for determining contamination in a contamination detecting apparatus, said contamination detecting apparatus comprising:

a light transmissive element that defines a surface;

a set of emitters arranged to emit beams of light into the light transmissive element wherein the beams of light propagate inside the light transmissive element while illuminating the surface such that surface contamination on the surface causes an attenuation of the propagating light; and a set of light detectors arranged proximal to the surface to receive light from the set of emitters on a plurality of light paths;

said method comprising:

determining, based on output signals from the light detectors, a transmission value for each light path in the plurality of light paths;

determining a first group transmission value for a first set of light paths in the plurality of light paths, wherein the first set of light paths share a first property;

determining a second group transmission value for a second set of lights in the plurality of light paths, wherein the second set of light paths share a second property;

generating a contamination value based on the first group transmission value with the second group transmission value; and displaying an indication of surface contamination based on the generated contamination value.

15. A non-transitory, tangible computer readable storage medium storing processing instructions that, when executed by a hardware processor, performs the method according to claim 14.

* * * * *